(12) United States Patent
Klaiman

(10) Patent No.: US 11,854,168 B2
(45) Date of Patent: *Dec. 26, 2023

(54) ARTIFACTS REMOVAL FROM TISSUE IMAGES

(71) Applicant: HOFFMANN-LA ROCHE INC., Little Falls, NJ (US)

(72) Inventor: Eldad Klaiman, Starnberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/054,337

(22) Filed: Nov. 10, 2022

(65) Prior Publication Data
US 2023/0064699 A1    Mar. 2, 2023

Related U.S. Application Data

(63) Continuation of application No. 16/646,048, filed as application No. PCT/EP2018/075708 on Sep. 21, 2018, now Pat. No. 11,521,301.

(30) Foreign Application Priority Data

Sep. 22, 2017    (EP) .................... 17192764

(51) Int. Cl.
*G06T 5/00*    (2006.01)
*G16H 30/40*    (2018.01)
(Continued)

(52) U.S. Cl.
CPC .............. *G06T 5/005* (2013.01); *G06N 3/04* (2013.01); *G06N 20/00* (2019.01); *G16H 30/40* (2018.01);
(Continued)

(58) Field of Classification Search
CPC ........... G06T 5/005; G06T 2207/20081; G06T 2207/20084; G06T 7/0012; G16H 30/40; G06N 20/00; G06N 3/04
See application file for complete search history.

(56) References Cited

U.S. PATENT DOCUMENTS

2013/0039556 A1    2/2013    Kachelriess et al.
2015/0030237 A1    1/2015    Jancsary et al.
(Continued)

FOREIGN PATENT DOCUMENTS

CN    104657962 A    5/2015
CN    104756151 A    7/2015
(Continued)

OTHER PUBLICATIONS

Agostinelli et al., "Adaptive multi-column deep neural networks with application to robust image denoising", NIPS'13, Dec. 10, 2013 (Year: 2013).*

(Continued)

*Primary Examiner* — Amandeep Saini
*Assistant Examiner* — Julius Chai
(74) *Attorney, Agent, or Firm* — HARNESS, DICKEY & PIERCE, P.L.C.

(57) ABSTRACT

The method includes generating, for each of a plurality of original images, a first artificially degraded image by applying a first image-artifact-generation logic on each of the original images; and generating the program logic by training an untrained version of a first machine-learning logic that encodes a first artifacts-removal logic on the original images and their respectively generated first degraded images; and returning the trained first machine-learning logic as the program logic or as a component thereof. The first image-artifact-generation logic is A) an image-acquisi- (Continued)

---

Applying an image-artifact-generation logic on each of a plurality of original images for generating artificially degraded images — 102

Training a machine-learning logic that encodes an artifacts-removal logic on the original and the degraded images — 104

Returning the trained machine-learning logic — 106 tion-system-specific image-artifact-generation logic or B) a tissue-staining-artifact-generation logic.

**22 Claims, 9 Drawing Sheets
(4 of 9 Drawing Sheet(s) Filed in Color)**

(51) Int. Cl.
*G06N 20/00* (2019.01)
*G06N 3/04* (2023.01)
(52) U.S. Cl.
CPC ............... *G06T 2207/20081* (2013.01); *G06T 2207/20084* (2013.01)

(56) References Cited

U.S. PATENT DOCUMENTS

| | | | |
|---|---|---|---|
| 2017/0071562 | A1 | 3/2017 | Suzuki |
| 2017/0213321 | A1 | 7/2017 | Matviychuk et al. |
| 2017/0249759 | A1 | 8/2017 | Hsieh et al. |

FOREIGN PATENT DOCUMENTS

| | | | |
|---|---|---|---|
| CN | 106803237 A | 6/2017 | |
| CN | 106952239 A | 7/2017 | |
| CN | 107122826 A | 9/2017 | |
| JP | 2015-104668 A | 6/2015 | |
| WO | WO-2010/119355 A1 | 10/2010 | |

OTHER PUBLICATIONS

Svoboda et al. "Generation of Digital Phantoms of Cell Nuclei and Simulation of Image Formation in 3D Image Cytometry", Cytometry Part A, 75A, 2009, pp. 494-509 (Year: 2009).*
Lehmussola et al. "Computational Framework for Simulating Fluorescence Microscope Images With Cell Populations", IEEE Trans Med Imaging, 26(7), 2007 (Year: 2007).*
Ortiz-de-Solorzano et al., "Toward a Morphodynamic Model of the Cell", IEEE Signal Processing Magazine, 20, Jan. 2015 (Year: 2015).*
Murphy, "Building Cell Models and Simulations from Microscope Images", Methods, 96, Mar. 2016. (Year: 2016).*
De Vos et al., "Focus on Bio-Image Informatics", Advances in Anatomy, Embryology, and Cell Biology, 2016 (Year: 2016).*
Lehmussola et al., "Synthetic Images of High-Throughput Microscopy for Validation of Image Analysis Methods", Proceedings of the IEEE, vol. 96, No. 8, 2008 (Year: 2008).*
Apou et al., "Synthesizing Whole Slide Images", ISPA 015, Sep. 7-9, 2015. (Year: 2015).*
International Search Report dated Nov. 19, 2018 in corresponding PCT Application No. PCT/EP2018/075708.
Written Opinion dated Nov. 19, 2018, in corresponding PCT Application No. PCT/EP2018/075708.
Ken Perlin, 'An Image Synthesizer' SIGGRAPH paper, ACM, vol. 19, No. 3, 1985, pp. 287-296.
V. Jain and H.S. Seung, 'Natural Image Denoising with Convolutional Networks' *Advances in Neural Information Processing Systems*, 2009.
J. Xie et al., 'Image Denoising and Inpainting with Deep Neural Networks' *Advances in Neural Information Processing Systems*, 2012.
F. Agostinelli et al., 'Adaptive Multi-Column Deep Neural Networks with Application to Robust Image Denoising' *Advances in Neural Information Processing Systems*, Dec. 2013.
J. Long et al., 'Fully Convolutional Networks for Semantic Segmentation' *Proceedings of the IEEE Conference on Computer Vision and Pattern Recognition*, 2015.
Lovedeep Gondara, 'Medical image denoising using convolutional denoising autoencoders' Simon Fraser University, ArXiv preprint arXiv:1608.04667, 2016.
O. Ronneberger et al., 'U-Net Convolutional Networks for Biomedical Image Segmentation' MICCAI 2015: 18th International Conference, Munich, Germany, Oct. 5-9, 2015, Proceedings, Part III, Springer International Publishing, ISBN=978-3-319-24574-4.
R. Gao and K. Grauman, 'On-Demand Learning for Deep Image Restoration' IEEE International Conference on Computer Vision (ICCV), Aug. 2017.
D. Eigen et al., 'Restoring an Image Taken Through a Window Covered with Dirt or Rain' IEEE International Conference on Computer Vision, Dec. 2013.
International Preliminary Report on Patentability dated Apr. 2, 2020, issued in corresponding International Application No. PCT/EP2018/075708.
Office Action dated May 10, 2022, issued in corresponding European Patent Application No. 18 769 411.2.
Notice of Reason for Rejection dated Jul. 5, 2021, issued in corresponding Japanese Patent Application No. 2020-514984.
Hu Chen et al., 'Low-Dose CT With a Residual Encoder-Decoder Convolutional Neural Network' *IEEE Transactions on Medical Imaging*, vol. 36, Issue 12, Dec. 2017, pp. 2524-2535.
Grégory Apou et al., 'Synthesizing Whole Slide Images' *9th International Symposium on Image and Signal Processing and Analysis (ISPA 2015)*, Sep. 2015, pp. 154-159.
Antti Lehmussola et al., 'Computational Framework for Simulating Fluorescence Microscope Images With Cell Populations' *IEEE Transactions on Medical Imaging*, vol. 26, No. 7, Jul. 2007, pp. 1010-1016.
Antti Lehmussola et al., 'Synthetic Images of High-Throughput Microscopy for Validation of Image Analysis Methods' *Proceedings of the IEEE*, vol. 96, No. 8, Aug. 2008, pp. 1348-1360.
Carlos Ortiz-de-Solórzano et al., 'Toward a Morphodynamic Model of the Cell' *IEEE Signal Processing Magazine*, Jan. 2015, pp. 20-29.
Robert F. Murphy, 'Building Cell Models and Simulations from Microscope Images' *Methods*, 96, Mar. 2016.
Evan Shelhamer et al. 'Fully Convolutional Networks for Semantic Segmentation' *IEEE Transactions on Pattern Analysis and Machine Intelligence*, May 2016.
Murphy, "Building Cell Models and Simulations from Microscope Images", Methods, 96, Mar. 2016.
De Vos et al., "Focus on Bio-Image Informatics", Advances in Anatomy, Embryology, and Cell Biology, 2016.
David Svoboda et al., "Generation of Digital Phantoms of Cell Nuclei and Simulation of Image Formation in 3D Image Cytometry," Cytometry Part A, 75A, 2009, pp. 494-509, Mar. 16, 2009.
First Office Action dated Mar. 15, 2023 in Chinese Application No. 2018800575452.
Office Action dated Jul. 21, 2023 in Chinese Application No. 201880057545.2.

* cited by examiner

ARTIFACTS REMOVAL FROM TISSUE IMAGES

CROSS-REFERENCE TO RELATED APPLICATIONS

This application is a continuation application of U.S. application Ser. No. 16/646,048, filed on Mar. 10, 2020, which is a national phase under 35 U.S.C. § 371 of PCT International Application No. PCT/EP2018/075708, which has an International filing, date of Sep. 21, 2018, which claims priority to European Patent Application No. 17192764.3, filed Sep. 22, 2017, the entire contents of each of which are hereby incorporated by reference.

FIELD OF THE INVENTION

The invention relates to image analysis, and more particularly to the removal of artifacts from tissue images.

BACKGROUND AND RELATED ART

In digital pathology, information encoded in a digital image of a tissue slide is extracted from the image for answering various biomedical questions, e.g. for assisting a health care professional in the diagnosis and treatment of diseases. The field of digital pathology is currently regarded as one of the most promising avenues of diagnostic medicine in order to achieve even better, faster and cheaper diagnosis, prognosis and prediction of cancer and other important diseases. Digital pathology techniques are also widely used in the context of drug development for assisting pathologists in understanding the tumor microenvironment, learning about patient response, drug mode of actions and other information available from the tissue images.

The scanned digital tissue images, especially in high magnifications, tend to have several types of noise related to both staining process and scanning process. These noise artifacts present a problem to both manual and automatic analysis. The artifacts can substantially affect and limit both automatic algorithm results and manual scoring by expert pathologists or at least make such manual or automatic scoring very difficult and inconsistent.

Various approaches exist for preprocessing tissue images for removing or reducing noise artifacts from the images. For example, Jain et al. (Jain, Viren, and Sebastian Seung. "*Natural image denoising with convolutional networks*" *Advances in Neural Information Processing System*, 2009) suggested applying convolutional neural networks, Xie et al. (Xie, Junyuan, Linli Xu, and Enhong Chen "*Image denoising and inpainting with deep neural networks*" *Advances in Neural Information Processing Systems*. 2012) used stacked sparse autoencoders for image denoising, Agostenelli et al. (Agostinelli, Forest, Michael R. Anderson, and Honglak Lee. "*Adaptive multi-column deep neural networks with application to robust image denoising*" *Advances in Neural Information Processing Systems*, 2013) used adaptive multi column deep neural networks for image denoising. Other approaches based on wavelets and Markov random fields have also been described.

US 2017/0213321 A1 describes a computer-implemented method for denoising image data. The method includes a computer system receiving an input image comprising noisy image data and denoising the input image using a deep multi-scale network comprising a plurality of multi-scale networks sequentially collected. Each respective multi-scale network performs a denoising process which includes dividing the input image into a plurality of image patches and denoising those image patches over multiple levels of decomposition using a threshold-based denoising process. The threshold-based denoising process denoises each respective image patch using a threshold which is scaled according to an estimation of noise present in the respective image patch. The noising process further comprises the assembly of a denoised image by averaging over the image patches.

RUOHAN GAO ET AL: "On-demand Learning for Deep Image Restoration", 2017 IEEE INTERNATIONAL CONFERENCE ON COMPUTER VISION (ICCV), August 2017 (2017 August) describes an examination of the weakness of conventional "fixated" models and demonstrates that training general models to handle arbitrary levels of corruption is non-trivial. In addition, an on-demand learning algorithm for training image restoration models with deep convolutional neural networks is described. The main idea is to exploit a feedback mechanism to self-generate training instances where they are needed most, thereby learning models that can generalize across difficulty levels.

A problem associated with the current denoising approaches is that the generation of the noise-removal logic involves a training phase of a machine learning logic on training data that is hard to obtain in the required quantity and quality: typically, images have to be annotated manually for generating a training data set in which noise artifacts and/or tissue structures which look similar to artifacts but which should not be identified as noise artifacts are labeled as "true artifacts" or "true tissue structures". This process is highly time consuming and requires many hours, days or even weeks of work of one or more experienced pathologists. Moreover, manual annotation of "real noise" and "real tissue" may be subjective and different pathologists may have different opinions regarding the nature of a particular image section that cannot surely be classified as artifact. Thus, the creation of artifact removal program logic currently requires the creation of training data sets which is very time consuming and therefore expensive.

Due to the high costs involved with the creation of a training dataset, the training data sets used in praxis are often hardly of sufficient size to allow for the generation of a noise removal program logic of sufficient accuracy, because the training of program logic that is able to accurately remove image artifacts typically requires a large training dataset that covers many different manifestations of a particular artifact type.

SUMMARY

It is an objective of the present invention to provide for an improved method of generating program logic configured for removing artifacts from digital tissue images and for a corresponding storage medium and image analysis system as specified in the independent claims. Embodiments of the invention are given in the dependent claims. Embodiments of the present invention can be freely combined with each other if they are not mutually exclusive.

In one aspect, the invention relates to a digital pathology method. The method comprises:

generating, for each of a plurality of original images respectively depicting a tissue sample, a first artificially degraded image by applying a first image-artifact-generation logic on each of the original images, the first image-artifact-generation logic being configured for specifically generating a first type of artifact; and generating a program logic configured for removing artifacts from digital tissue images. The generation of the program logic comprises:

training an untrained version of a first machine-learning logic that encodes a first artifacts-removal logic on the original images and their respectively generated first degraded images; and returning the trained first machine-learning logic as the program logic or as a component thereof.

The artifact generation logic can in particular be an image-capture-device specific artifact-generation logic ("option A") or a staining protocol related artifact ("option B").

Said features may be advantageous, because the training dataset comprising "true artifact-free" and "true artifact-containing" images can be created fully automatically. Thus, a very large training dataset can be generated. Typically, high quality images which are basically free of any artifacts or at least free of artifacts of a particular type can be obtained comparatively easy. For example, artifacts resulting from dust in the optical system of a camera can be avoided simply by using a microscope whose optical system is basically free of dust grains. This microscope can be used for capturing hundreds and thousands of images of different tissues stained with different stains according to different staining protocols. Thus, a large number of "true noise-free training images" can be captured easily, and a corresponding number of "true noise-containing training images" can be created from the former automatically by applying the image-artifact-generation logic.

Moreover, as the creation of the training images including the degraded, "noisy" training images is performed automatically, the generated training data set may be larger than a manually annotated training data set, because high-quality, noise free images can typically obtained easily. Thus, the accuracy of the trained machine learning logic may be higher.

In a further beneficial aspect, inconsistencies in the annotations in the training data set inherent to the manual annotation process may be avoided, because the artifacts in the training images are created automatically and the artifact generation algorithm "knows" at which region in an image an artifact was created.

According to embodiments, the plurality of original images comprises images depicting tissues derived from many different tissue types and/or depicting tissues having been stained with many different stains and/or depicting tissues having been stained according to many different staining protocols and/or depicting tissues whose image was captured by many different image capturing systems and/or depicting tissues in many different resolutions.

In some embodiments, the automated generation of the degraded version of an image is performed by a "image degradation" application used for generating a training data set that is separate from the program logic used for artifacts removal.

In other embodiments, the automated generation of the degraded version of an original image is performed by the machine learning algorithm that is trained to "learn" to remove the artifact. In this case, a machine learning logic can be used for "learning" one or more artifacts removal logics, whereby only the original images are input into said machine learning logic during the training as well as during the test phase. The machine learning logic is configured to operate in two different modes, the training phase mode and the test phase mode. Selectively in the training phase mode, this machine learning logic will automatically generate the degraded image versions from the original images received as input. In the test phase mode, the trained machine learning logic will merely remove the artifacts from the original images received as input. The two different functionalities may be implemented in different modules of the machine learning algorithm. For example, the automated generation of the degraded image version can be performed by a particular layer of a neural network, whereby one or more other layers of said network are used and trained to remove said artifact from an image.

Acquiring high-quality tissue images which are basically free of noise artifacts from many different tissues and/or from many different image capturing devices and/or from tissue sections subjected to many different conditions and then automatically deriving a "degraded", noisy version of said image can typically performed much faster and easier than annotating a training data set having the same broad coverage manually. Thus, a machine learning algorithm trained to remove artifacts from the above described automatically generated data set may be more accurate and more robust against variations regarding the tissue type, the stain, the staining protocol and the like because of the increased size and diversity of the training data set.

According to embodiments, the training of the untrained version of the first machine-learning logic comprises inputting the original images and their respectively generated first degraded images into the untrained version of the first machine-learning-logic. Each of the first degraded images is annotated as artifact-afflicted version of a respective one of the original images. The first machine learning logic encodes a first artifacts-removal logic. The training is performed by applying the first artifacts-removal logic on the first degraded images for generating a first reconstructed image from each of the first degraded images and by automatically modifying the first artifacts-removal logic such that deviations of the first reconstructed images from the original images from which the first reconstructed images were derived are minimized.

This "error function minimization" approach for training the artifacts removal logic is in generality called "supervised learning" machine learning. Supervised machine learning techniques may be implemented in various forms, e.g. as a neural network based machine learning logic, as support vector machine based machine learning logic, or the like.

According to embodiments, the method further comprises generating, for each of the original images, a second artificially degraded image. The second artificially degraded image is generated by applying a second image-artifact-generation logic on each of the original images. The second image-artifact-generation logic is configured for specifically generating a second type of artifact. The generation of the program logic further comprises: training an untrained version of a second machine-learning logic that encodes a second artifacts-removal logic on the original images and their respectively generated second degraded images; and combining the trained first machine-learning logic with the trained second machine-learning logic for providing the program logic; the generated program logic is configured for removing artifacts of at least the first and the second artifact type. Alternatively, the first and second machine-learning logics can be part of the same machine learning architecture that is trained in a single training step on a training data set comprising both the first and second degraded images.

Training one or more machine learning logics on two separate sets of artificially degraded images may be advantageous in case an artifact removal logic shall be generated which is capable of selectively removing artifacts of a particular type from an image. For example the generated artifacts removal logic may be integrated in an image analysis software package that is sold together with or for use in combination with a particular microscope. The software may allow the user of the software to select one or more artifacts types, e.g. "blur artifacts", "focus artifacts", "dust", etc. for selectively removing artifacts of a particular type from an image. As the artifact-removal logics have been trained separately on different training data sets respectively representing the different types of artifacts, the software may allow the user to selectively select and use e.g. the first artifacts-removal logic or to selectively select and use the second artifacts-removal logic.

In some embodiments, the artifacts removal logic is applied in real time during image acquisition, e.g. during an image scanning process. Thus, during the image acquisition process, for each acquired image, a "clean" version is generated by applying one or more artifacts removal algorithms on the currently acquired image. In other embodiments, one or more artifacts removal logics are applied on already acquired images, e.g. on images having been acquired in the past and having been stored in the form of an image library on a storage medium.

Thus, in some embodiments, combining the trained first machine-learning logic with the trained second machine-learning logic for providing the program logic may comprise combining two separately addressable and separately callable trained program logics into the same software application program. In other embodiments, the combination may be an integral part of the training process. For example, a single machine learning software may be trained on a data set comprising the original images and a mixture of the first and the second degraded images.

Combination of multiple artifact generation logics and the generation and training of respective artifact removal logics may be advantageous as in reality, combinations of multiple different artifacts are frequently observed. In some embodiments, the degraded image generated by one artifacts-generation-logic is input to at least one further artifacts generation logic of a different type to generate a two-fold (or, if further artifact-generation-logics are applied, a multi-fold) degraded image. This may allow the generation and training of an artifacts-removal-logic adapted to remove artifacts of many different types from an image in a stepwise manner.

For example, the returned artifacts-removal logic can be configured such that it at first removes bad-focus noise such as blur and then removes line noise and speckle noise caused by physical obstructions such as hair, dust, etc. Finally, the artifacts-removal logic can remove staining artifacts such as non specific staining. Accordingly, the first artificially degraded images could comprise artifacts which simulate blurring artifacts and the second artificially degraded images could comprise artifacts which simulate a non-specific staining artifact. Optical noise such as blur does typically not depend on types of noise such as the presence of undesired physical objects (e.g. hair, dust) in the image. However, in some cases, the undesired physical objects may cause an autofocus mechanism to select the wrong focus layer. Moreover, the speckle noise may be affected by the bad-focus noise in case the bad-focus noise results in a blurring of the tissue section as well as of the speckles. Thus, the relationships between artifacts of different types is complex and a challenge for any artifact removal approach.

Due to the time and effort needed for manually annotating image data sets, the size of training data sets comprising annotated tissue images with and without artifacts or with combinations of different artifacts is typically small compared to the wide range of combinations of artifacts that can be observed in reality. Thus, the use of manually annotated training data sets inherently bears a strong risk of over-fitting during training. By computationally generating many different types of artifacts in many different combinations, the risk of over-fitting may be avoided or at least reduced.

According to embodiments, the second machine learning logic is trained by inputting the original images and their respectively generated second degraded images into an untrained version of the second machine-learning-logic, whereby each of the second degraded images is annotated as artifact-afflicted version of a respective one of the original images. The second machine learning logic encodes a second artifacts-removal logic. The training is performed by applying the second artifacts-removal logic on the second degraded images for generating a second reconstructed image from each of the second degraded images and by automatically modifying the second artifacts-removal logic such that deviations of said second reconstructed images from the original images from which said second reconstructed images were derived are minimized. Thus, also the second machine-learning logic and/or any-machine learning logic encoding a multi-step-artifacts-removal logic described further below may be trained such that an error function being descriptive of a deviation of the original image and the result of applying an image reconstruction logic on a degraded image is minimized.

In some embodiments, the second machine learning algorithm comprises a sub-module that automatically generates the artifact-afflicted version of the original images as described for embodiments above or is a sub-module of a machine learning logic that comprises a further sub-module configured to automatically generate the artifact-afflicted version of the original images. Thus, the expression "inputting a degraded (artifact afflicted) version of an original image" also includes the option that the degraded version is generated by a software logic that is bundled with the second program logic into a single executable program logic.

In some embodiment, the first, the second and any further machine-learning logic for removing artifacts of one or more artifact types is implemented in the same machine learning logic, e.g. in the same instance of a neural network. For example, irrespective of whether one machine learning logic is trained per artifacts type or whether the same machine learning logic is trained on training data comprising artifacts of two or more different artifacts types, neural networks can be used as the machine learning logic to be trained.

For example, the number of networks that are employed for training the respective artifacts generation logics and artifacts removal logics can be determined by trial and error. If a network architecture comprising a single neural network does not perform well, the network architecture may be extended to two networks or three networks or a different network layer architecture. Alternatively, multiple different network architectures are trained in parallel and the results generated by the trained networks on test images are combined and aggregated to generate a consolidated result of multiple networks that has a higher accuracy than the results obtained from any of them separately ("ensemble method" or "ensemble learning"). According to preferred embodiments, the method comprises providing a GUI to a user, the GUI enabling the user to select one or more of a set of predefined artifacts types and a corresponding set of selected artifacts removal logics to be applied automatically on any original image to be processed.

According to embodiments, the program logic configured for removing artifacts that is to be generated is a program logic configured for removing at least a number N different artifacts types from the digital tissue images. The number N is an integer larger than 1. The method further comprises: providing, for each of the N different artifacts types, a respective artifact-generation logic configured for specifically generating said particular type of artifact; applying, according to a first sequence, the number N different image-artifact-generation logics on the original images; thereby, the first image-artifact-generation logic within the first sequence takes each of the original images as input and outputs a degraded version of said image; the degraded image output by the first and any subsequent image-artifact-generation logic is used as input image by the next one of the N different image-artifact-generation logics in the first sequence; thereby, for each of the original images, a first multi-fold degraded image is generated. The generation of the program logic further comprises training a machine-learning logic that encodes a multi-step-artifacts-removal logic on at least the original images and their respectively generated first multi-fold degraded images; and using said trained multi-step-artifacts-removal logic for providing the program logic or for providing a part of the program logic that is to be generated.

According to some embodiments, the machine-learning logic that encodes a multi-step-artifacts-removal logic is an untrained machine learning logic that uses the output generated from a plurality of other machine learning logics for learning to correctly remove multiple different types of image artifacts. The other machine learning logics have respectively been trained to remove a particular type of image artifact.

In some embodiments, the trained multi-step-artifacts-removal logic is combined with the trained first machine-learning logic for providing the program logic. The resulting program logic is configured for sequentially removing artifacts of each of the N types of artifacts. The removal is preferably performed in accordance with the reverse order of the first sequence. The training of the machine-learning logic for providing the trained multi-step-artifacts-removal logic is performed such that the multi-step-artifacts-removal logic reconstructs the original image from the multifold-degraded training images. For example the multi-step-artifacts-removal logic may be configured to call any of the first or second ("single-artifact")-machine-learning logics in different orders and may be configured to learn a sequence of artifact removal operations that is best suited to reconstruct an image that is very similar or identical to the original image.

For example, the number N may be "3" and the first sequence may comprise the following types of artifacts in the following order: a) "overstaining", b) "dust artifacts" and c) "blurring artifacts".

Applying multiple artifact-generation logics sequentially on the degraded image respectively provided by the previously called artifact generation logic and training an artifact removal logic such that it reconstructs the original image from the multifold-degraded training images may be advantageous as in praxis, an image may comprise artifacts of many different types, whereby an artifact may be overlaid by, distorted or otherwise affected by a later introduced type of artifact. Thus, the artifacts removal logic may be trained such that it is capable of identifying and compensating also a sequence of image artifacts of different types and thus may be able to compensate also complex combinations of artifacts of different types commonly observed in praxis in digital pathology. According to embodiments, the intermediate images created in each degradation step defined by a sequence of artifact-generation logics are respectively used as "auxiliary loss" in the network. This means that during training not only the last output of the net is compared to the clean image, but in one or more places along the processing layers an additional output image ("intermediate image") is created by the network (during training only) and compared to the original image to create a loss that drives the training of the preceding layers. For example, a first auxiliary loss image (a first intermediate image) of the partially degraded image (e.g. without blur/defocus) could be computed by applying the blur-artifact-removal algorithm on the received image, and for each of the subsequent artifacts removal logics in the sequence, an corresponding next "auxiliary loss"/intermediate image is obtained by applying a respective one of the artifacts removal algorithms on the intermediate image generated in the previous step until the last loss at the real "deploy" output of the net is the clean image (which should be free of all artifacts belonging to an artifact type of the above mentioned artifacts removal sequence).

According to some embodiments, the method further comprises applying, according to at least a second sequence, the number N different image-artifact-generation logics on the original images. Thereby the first image-artifact-generation logic within said second sequence takes each of the original images as input. The degraded image output by the first and any subsequent image-artifact-generation logic is used as input image by the next one of the different image-artifact-generation logics in the second sequence. Thus, by executing each of the image-artifact-generation logics in the second sequence, for each of the original images, a second multi-fold degraded image is created. Thus, in this embodiment, for each original image, a first multi-fold-degraded image is obtained by sequentially applying the image-artifact-generation logics according to the first sequence as described above. In addition, one second multi-fold-degraded image is obtained per original image by sequentially applying the image-artifact-generation logics according to the second sequence as described above. The first and second multi-fold-degraded image may differ from each other, because the sequence of applying the image degradation algorithm typically has an impact on the resulting image. For example, a depicted grain of dust may have sharp edges if the dust artifact is added after a blurring artifact was added to an image and may have blurred edges if the blurring artifact was added after the dust artifact.

According to preferred embodiments, the training of the machine-learning logic that encodes a multi-step-artifacts-removal logic is performed on at least the original images and their respectively generated first and second multi-fold degraded images.

This may be advantageous, because two or more different sequences of artifacts generation are covered in the training data set and the resulting trained artifacts removal logic will be capable of compensating multiple different sequences of generating artifacts in an image. This may be highly useful for compensating complex combinations of multiple different artifact types where the actual sequence of artifact generation is unknown or heterogeneous. For example, partial overstaining artifacts in some image regions may later be blurred as the result of an out-of-focus artifact. In addition, or alternatively, or selectively in some image regions, the overstaining artifacts may be overlaid by dust artifacts resulting from dust particles on the lenses of a microscope. So the number and type of artifact combinations may vary within an image.

Sometimes, the actual physical order of artifact introduction is unclear or unknown. For example, dirt and debris particles on a tissue section, e.g. hair, cloth fibers or the like, may cause the image acquisition system to select a wrong focus layer. As a consequence, the dirt may be in-focus while all other parts of the image comprise an out-of-focus artifact and appear blurred. In other images, the dirt may not be the cause of an out-of focus error. Rather, an out of focus error may occur due to a wrong configuration of the camera system. In this case, the tissue as well as the dirt particles will show an out-of focus error and both the tissue and the dirt will appear blurred. By training the machine learning logic not only on different types of artificially created artifact types, but also un multiple different artifact generation sequences, it may be ensured that the training data set covers the huge combinatorial space of artifact combinations which are observed in praxis. It should be noted that manually annotated training data sets typically consist of annotated images which were all derived from a very small number of experimental settings and image acquisition systems. Thus, the manually annotated data sets typically do not reflect the combinatorial complexity and heterogeneity of artifact type combinations that is observed in different image acquisition systems using different staining protocols, and different tissue types. Thus, manually annotated data set often resulted in the generation of artifact removal algorithm which were not universally applicable for many different types of microscopes, different types of lenses and/or staining protocol. To the contrary, embodiments of the invention may allow to automatically generate an artifacts removal logic that has been trained on a training data set that covers a huge diversity of artifact types and a huge diversity of sequential artifact combinations. This may be of particular use e.g. for image analysis software that is designed for a wide range of users, e.g. pathologists, molecular biologists, workers in the field of quality management and production, etc.

According to embodiments, the method comprises automatically creating a plurality of sequences of the number N different image-artifact-generation logics. The plurality of sequences comprise the first, the second and at least a third sequence by permutating the positions of the image-artifact-generation logics. The method further comprises applying, for each of the plurality of sequences, the number N different image-artifact-generation logics of said sequence on the original images, whereby the first image-artifact-generation logic within in said sequence takes each of the original images as input; the degraded image output by the first and any subsequent image-artifact-generation logic in said sequence is used as input image by the next one of the different image-artifact-generation logics in said sequence, thereby generating, for each of the original images and for each of the plurality of sequences, a multi-fold degraded image. The training of the untrained version of the machine-learning logic that encodes a multi-step-artifacts-removal logic is performed on at least the original images, the plurality of sequences and their respectively generated multi-fold degraded images.

The automated sequence generation may be advantageous, because it allows to cover a huge combinatorial space of artifact type combinations. For example, the number N may be "3" and the set of artifact types to be covered may comprise artifact types AF1, AF2 and AF3. The permutation of the three artifact types will result in an automated generation of the following sequences S1 to S6:
S1: AF1, AF2, AF3
S2: AF1, AF3, AF2

S3: AF2, AF1, AF3
S4: AF2, AF3, AF1
S5: AF3, AF1, AF2
S6: AF3, AF2, AF1

By applying each of the above 6 artifact generation logics on a particular input image I, 6 multi-fold degraded images will be generated for said image. In addition, in some embodiments, also three single-fold degraded images may be generated and fed into the machine learning logic, whereby each of the single-fold-degraded image may be generated by applying either AF1, or AF2 or AF3 on the original image.

So for 100 original images and for 3 different types of artifacts, 6 sequences S1-S6, 600 multi-fold degraded images and three single-fold degraded images will be created from each original image and will be fed into the machine learning algorithm.

In some embodiments, the permutation of the artifact types comprises generating sequences which comprise only a sub-set of the available artifact-generation-logics. In the depicted example, those additional sequences would comprise:
S7: AF1, AF2
S8: AF1, AF3
S9: AF2, AF1,
S10: AF2, AF3
S11: AF3, AF1
S12: AF3, AF2

So for 100 original images and for 3 different types of artifacts, 12 sequences S1-S12, 1200 multi-fold degraded images and three single-fold degraded images will be created from each original image and will be fed into the machine learning algorithm.

As can be inferred from the above depicted examples, the combinatorial space is huge. Thus, embodiments of the invention may allow generating a training data set that covers much more artifact combinations than any manually annotated data set could cover.

In some embodiments, the length of the generated sequences is limited to a chain length of a predefined maximum size, e.g. two, three or four elements. This may increase performance.

In addition, or alternatively, only a single sequence or a few (less than four sequences) of applying artifact-generation-logics are defined manually. This single sequence (or each of the few sequences) in this case represent the typical sequence of artifact generation in a tissue staining and image acquisition workflow. This embodiment may increase the performance by reducing the combinatorial space and may be suited for application scenarios where the typical sequence of artifact generation is known in advance.

According to some embodiments, a GUI is provided that enables a user to select one or more different types of artifact removal logics, thereby enabling the user to manually specify a sequence of artifacts removal logics to be applied on an input image. According to preferred embodiments, however, the sequence of artifact-removal logics to be used by the trained multiple-artifacts-removal logic is learned in a machine learning process and is encoded in the trained multiple artifact-removal logic.

According to embodiments, the first and/or second machine-learning logic and/or the machine-learning logic that encodes the multi-step-artifacts-removal logic is a neural network. In some embodiments the first and/or second machine-learning logic and/or the multi-artifact machine-learning logic belong to the same single neural network. In other embodiments, the first and/or second machine-learning logic and/or the multi-artifact machine-learning logic are implemented in a separate network, respectively, and the networks are combined in a "super" neural network or in another form of software logic that is adapted to integrate the results provided by the individual networks. For example, the "super" neural network could be trained to automatically combine the output of the individual networks such that many different types of artifacts are removed and whereby the "super" network coordinates the operation of the individual network for removing different types of artifacts.

According to embodiments, the first and/or second machine-learning logic and/or the machine-learning logic that encodes the multi-step-artifacts-removal logic is an autoencoder.

According to embodiments, the first and/or second artifact is selected from a group comprising: staining artifact; scanning artifact; tissue-fold artifact; line-artifact (e.g. air bubbles, fibers).

Typically, when feeding the machine-learning logic with training data comprising the original images and the degraded versions of the images which selectively comprise the artifacts of one of the artifact types, the artifacts-removal logic generated for each of said artifact types respectively is configured for selectively removing artifacts of said single type.

According to embodiments, the scanning artifact is selected from a group comprising bad-focus-artifacts (e.g. blurred images resulting e.g. from an erroneous selection of the focus layer or from a misconfiguration of a microscope), stitching-artifacts (e.g. effects and patterns resulting from scanner-stitching) and speckle-noise-artifacts (e.g. dust in the optics of the image acquisition system, bad pixels caused by defects in the sensor hardware of the camera).

According to embodiments, the staining artifact is selected from a group comprising background-staining artifact, non-specific staining artifact, residual staining artifact, anthracotic pigment artifact.

According to embodiments, the first and/or second image-artifact-generation logic is configured to specifically generate bad-focus-artifacts by applying a point spread function (PSF) or an approximation, e.g. a Gaussian approximation, of the point spread function on each of the original images.

For example, the PSF and/or the Gaussian approximation ("Gaussian blurring") is applied locally on the image. For example, all pixel blobs having an intensity above a predefined threshold can be identified and the PSF can be applied on each of the identified pixel blobs for generating a degraded image comprising "blurred" blobs which simulate the blurring generated by the selection of a wrong focus layer.

According to embodiments, the PSF is generated by mounting micro-beads of a known size on an empty tissue slide or on a tissue slide together with or in addition to the tissue sample; for example, the micro-bead size can be chosen such that the expected size of the micro-bead depicted in a digital image of the tissue slide is one pixel or a defined set of pixels. The expected size of the depicted bead will depend on the size of the bead, the magnification, resolution and/or other properties of the image acquisition system; then, the image acquisition system captures a digital image of the slide with the tissue sample and the micro-beads; the obtained digital image is referred to in the following as "calibration image"; an image analysis system analyzes the obtained calibration image for measuring the size of the image area that actually depicts the bead; the image analysis system also acquires the pixel pattern observable within the image area that actually depicts the bead and fits a mathematical model to that pattern for generating a PSF; the PSF is configured to generate the extracted pattern if applied on an image blob having the size of the expected bead-area.

The generated PSF is then integrated into a machine-executable code, e.g. a Java or C program code, for providing an image-artifact-generation logic adapted to generate speckle noise artifacts which reproduce the speckle noise generated by a particular image acquisition system or image acquisition system type. The PSF of the image-artifact-generation logic can then be applied on each high-intensity blob of an original image for creating a degraded image that simulates a bad focus artifact for each or at least some of the high intensity blobs of the original image. A "high intensity blob" as used herein is a region of adjacent pixels whose intensity is significantly higher than the intensity of the surrounding pixel area. For example, the high intensity blobs can be identified by applying an intensity threshold or similar image processing and segmentation operations. Instead of the PSF, a Gaussian filter model could likewise be created by fitting mathematical functions to an image deterioration generated by a particular image acquisition system. A Gaussian filter can be considered as a "simple" approximation for the PSF and is be applied in a similar manner.

This may be advantageous as bad-focus errors frequently occur in digital pathology and the PSF based artifact-generation logic has been observed to faithfully reproduce this type of artifact.

According to embodiments, the method comprises generating the PSF or the Gaussian filter empirically as described above for each of a plurality of different image acquisition systems (e.g. microscopes or slide scanners) or image acquisition system types (e.g. microscopes or slide scanners of a particular device type). Each of the PSFs (or Gaussian filters) is integrated into a respective artifact-generation-logic, which is in the following referred to as "image acquisition system specific artifact-generation-logic, IASS-artifact-generation-logic, or image acquisition type specific artifact generation logic—IATSS-artifact-generation-logic.

According to embodiments of the invention, the method for generating an artifact removal logic is performed for each of a plurality of different image acquisition systems (IASs). This means that from each of the IASs, a set of calibration images is obtained and a PSFs (or Gaussian filter) is obtained for each of the IASs by fitting a mathematical function such that the deviation of the measured shape and size of the beads to the expected size and shape of the beads is described (modeled) by the fitted function. The generated PSF (or Gaussian filter) is integrated in an artifact-generation-logic, thereby generating an IASS artifact-generation-logic adapted to simulate (bad-focus) noise artifact specifically generated by each of the plurality of IASs respectively. By applying the IASS artifact-generation-logic on original images or on images having been degraded by one or more other artifact-generation-logics, it is possible to generate a training dataset that simulates the out of focus errors generated by a particular IAS. Moreover, these "simulated" out-of-focus errors may be combined with one or more other artifact types, thereby generating a set of training images that faithfully reproduce the spectrum of artifacts that may be obtained by using a particular microscope.

According to other embodiments, the method for generating an artifact removal logic is performed for each of a plurality of different IAS types. The method is performed like the method for generating an artifact removal logic for each of a plurality of different image acquisition systems (IASs) described above, with the difference that multiple IAS of the same type are used for generating a pool of calibration images and that a single PSF (or Gaussian filter) for all IAS of the same type, whereby the single PSF (or Gaussian filter) is generated such that it simulates (bad-focus) an averaged noise artifact generated by all IAS of the same IAS type.

As a result, an image artifact removal logic is generated for each of the IAS types that is capable of compensating the bad-focus artifacts generated specifically by this particular IAS type. This may be particularly advantageous for manufacturers of microscope systems, slide scanners or other forms of image acquisition systems as the artifacts generated by a particular IAS type may be faithfully reproduced and may be used for automatically generating noise-removal logic that is capable of compensating bad focus artifacts generated by a particular type of IAS.

According to embodiments, the first and/or second image-artifact-generation logic is configured to specifically generate tissue-fold-artifacts in each of the original images, the generation of a tissue-fold-artifact comprising:

generating at least two image parts of the original image by cutting the original image across a randomly selected line;

overlaying the at least two image parts along the line; and merging the overlap, e.g. using alpha blending.

According to embodiments, the first and/or second image-artifact-generation logic is configured to specifically generate speckle-noise-artifacts by applying a salt-and-pepper noise function on each of the original images.

For example, applying a salt-and-pepper noise function on an input image can comprise:

generating, for each pixel in the input image, a random value, e.g. between 0 and 1;

specifying a salt-and-pepper noise threshold (e.g. 0.1 for a probability of 10% for a pixel to be affected by the speckle-noise);

determining, for each pixel in the input image, if the random value generated for the pixel is smaller than the salt-and-pepper noise threshold;

if true (the random value is smaller than the threshold), the pixel is replaced by a black or white pixel; in some embodiments, the replacement step is performed as an obligatory step, in other embodiments, the replacement step is performed only at a predetermined probability, e.g. 30%.

After a pixel was replaced by a black or white pixel in the previous step, the pixel is in some example implementations grown to a bigger size; for example, the pixel can be extended by randomly selecting a radius within a predefined radius range, e.g. 1-5 pixels, and setting all pixels within the radius around the replaced pixel to the same intensity value (black or white) as the intensity value of the replacement pixel.

Thus, black or white speckles of variable sizes can be obtained. The speckles represent dust speckles, bad pixels (as generated by defect CCD elements of a camera) and other forms of impulse noise sometimes seen on images. This noise is typically characterized by sharp and sudden disturbances in the image signal that presents itself as sparsely occurring white and black pixels. While state of the art approaches used median filters or morphology filters for noise removal, this approach is based on using a function that simulates the noise and training a machine learning logic on original images and speckle-noise images for automatically removing speckle-noise-artifacts. It has been observed that this approach is often more accurate and is more generic. In particular, as the noise is simulated, large training data sets can be generated which cover any possible combination of different noise artifact types, whereby one or even more chronological sequences of noise artifact generation may be covered. For example, noise speckles resulting from dust in the camera optics may not be affected by out-of-focus errors while noise speckles resulting from dust on the tissue slide will be affected from out-of-focus errors.

According to embodiments, the first and/or second image-artifact-generation logic is configured to specifically generate line-artifacts. A "line artifact" as used herein is an image artifact that has the shape of a curved or straight line. For example, line artifacts can be caused by cloth fibers or the outline of gas bubbles under the coverslip of a tissue slide. The generation of the line-artifacts comprises generating a plurality of polynomial curves using randomly generated values as curve parameters; and inserting black lines along the coordinates of the polynomial curves in each of the original images. Preferably, the thickness of the inserted lines represents the typical line thickness of physical objects expected to cause the line artifacts in a digital image captured by an IAS like a microscope or a slide scanner under a given magnification. Said physical objects can be, for example, cloth fibers, hair and/or gas bubble outlines. According to embodiments, the image-artifact-generation logic is configured to specifically generate line-artifacts whose length, thickness and/or curvature represents different types of physical objects, e.g. hair, gas bubble outlines and/or cloth fibers.

For example, the typical width of a hair is between 0.05 to 0.1 mm. Given a magnification of the IAS of 10×, the line thickness of the inserted line is in the range of 50-100 pixels for simulating "hair-related" line artifacts. In some examples, the polygon has a curvature degree of 0-3°. It has been observed that, at least when generating degraded training images with limited size (e.g. 512×512 pixels), a small curvature is sufficient to faithfully reproduce the curvature of most types of fiber-shaped artifacts.

According to embodiments, the first and/or second image-artifact-generation logic is configured to specifically generate stitching artifacts. The generation of the stitching artifacts comprises: scanning an empty slide using an IAS (in particular a slide scanner) whose stitching artifacts shall be removed; automatically analyzing the scanned image of the empty slide for generating a square filter that, when applied on an image with homogeneous intensity distribution, generates the measured stitching elements; generating a stitching-artifact-generation-logic by integrating the square filter in an executable program logic. The generated stitching-artifact-generation-logic can then be used as the first or second artifact-generation-logic for generating stitching artifacts typically produced by the image acquisition system or by a particular type of image acquisition system.

According to other embodiments, a two-dimensional function is defined ad-hoc to simulate the typical kind of stitching artifacts which in many cases result from a non-homogenous intensity distribution across the field of view of a specific tile. This two-dimensional function is then applied to the original image of the empty slide to generate a non-homogenous mean intensity along the original image. For example, the application of the function for generating a new, degraded image with a stitching artifact can be performed in accordance with the following formula:

$$Z=[C+0.5*(X/a-\text{floor}(X/a)+Y/b-\text{floor}(Y/b))]/[1+C];$$

$$\text{new\_image}=\text{original\_image}*Z.$$

Thereby, X is the image width coordinate having a value between 0 and image_width; Y is the image height coordinate having a value between 0 and image_height; a is the desired (predefined) tile artifact width; b is the desired (predefined) tile artifact height; Z is the resulting "tile artifact factor image" consisting of a grid of tiles with width a and height b; C is a "minimum darkness factor" chosen such that C/(1+C) is the lowest quantity by which an original image pixels is multiplied. The parameter orig_image is the original untiled image and "new_image" is the output image with the tiling artifact.

For example, the factor C can be chosen such that at the right lower corner of each grid element a factor of 0.1 (C is 1/9) is applied to the pixel intensities of the original image and at the left upper corner of each grid element, no additional intensity is applied to the pixel intensities of the original image (factor 1).

If C would be chosen to be "1", then the pixel of the top-left corner of each grid element would be 0.5*original pixel value. If C would be chosen to be "0" than the top-left pixel of each grid element would be 0. In other embodiments, the XY-axes definition may differ and the gradient produced by the above mentioned formula goes in opposite direction.

For example, a and be can be selected according to specifications of the image acquisition system used. For a 20× scan with the Ventana HTScan system, the parameter a may have the value 1658 and the parameter b may have the value 1152. An artificially degraded image comprising stitching artifacts generated in accordance with the above function is depicted in FIG. 9.

The method comprises applying the square filter on each of the original images for respectively obtaining the degraded version of the original image. The degraded version of the original image (or any other form of input image provided) will show the stitching artifact generated by this particular IAS.

For example, the application of the square filter on an input image comprises virtually dividing the image to squares of a width and height equal to the observed stitching artifact width and height and then multiplying the intensity values of the pixels of the stitching artifact square with the pixel intensities of each of the squares of the input image onto which the square filter is mapped and applied. Thereby, a pattern of corrupted, "degraded" squares is generated that simulates the stitching effect of the IAS or IAS type for which the square filter was generated.

According to embodiments, the first and/or second image-artifact-generation logic is configured to specifically generate non-specific-staining artifacts. The generation of the non-specific-staining artifacts comprises performing an operation selected from a group comprising:
  generating a color-noise function, the color noise function being a color-specific salt-and-pepper function or an empirical heuristics derived from images of tissue slides with regions with residual stain;
  applying the color-noise function on each of the original images, thereby generating, for each of the original images, a degraded image with non-specific-staining artifacts.

Automatically generating non-specific staining artifacts for generating a training data set with degraded, "virtually", non-specifically stained training images and training an artifacts removal algorithm on said training data set may be advantageous, as non-specific staining artifacts are complex noise patterns that often represent obstacles fur further image analysis. Non-specific staining artifacts are artifacts created by staining dyes that were not washed out during the staining process. The remaining dyes create patches of various sizes with a specific color of the dye. The colors used for this error are collected from the images that need to be denoised according to the dyes used in the tissue staining process For example, the application of a color-noise function having the form of a color-specific salt-and-pepper function noise function on an input image comprises:
  generating, for each pixel in the input image, a random value, e.g. between 0 and 1;
  specifying a salt-and-pepper noise threshold (e.g. 0.1 for a probability of 10% for a pixel to be affected by the non-specific-staining noise);
  determining, for each pixel in the input image, if the random value generated for the pixel is smaller than the salt-and-pepper noise threshold;
  if true (the random value is smaller than the threshold), the pixel is replaced by a pixel of the specific color of the color-specific salt-and-pepper function; this color is typically the color of the for which a respective image artifact training data set is to be created and for whose non-specific staining artifacts a respective stain specific artifacts-removal logic shall be created; in some embodiments, the replacement step is performed as an obligatory step, in other embodiments, the replacement step is performed only at a predetermined probability, e.g. 30%.

According to other examples, a color-noise function which is based on the "Perlin noise generator" approach is generated and used for generating degraded image versions comprising the non-specific-staining noise. Perlin noise is a type of gradient noise developed by Ken Perlin (SIGGRAPH paper "An image Synthesizer", 1985. The Perlin noise generator is a technique used to produce natural appearing textures on computer generated surfaces for motion picture visual effects. The development of Perlin Noise has allowed computer graphics artists to better represent the complexity of natural phenomena in visual effects for the motion picture industry. It has been surprisingly observed that Perlin noise also can be used for faithfully reproducing unspecific staining artifacts of certain dyes.

According to embodiments, the first and/or second image-artifact-generation logic is configured to specifically generate hue shift artifacts that are generated by a particular image acquisition system, the method further comprising:
  taking, by the image acquisition system, a digital image of an empty slide;
  analyzing the digital image of the empty slide for automatically generating a hue shift filter that is configured to simulate the hue-shift artifact generated by the image acquisition system; of course, this and the previous step may also be applied on many digital images of an empty slide to improve the data basis used for generating the hue shift filter; and
  applying the hue shift filter on an input image, thereby generating a degraded version of the input image.

This may be advantageous, as IAS-device specific chromatic aberrations and/or intensity shifts and/or device-specific blur effects can be corrected in a piece of software logic. For example, the software program typically provided in combination with an image acquisition system may comprise the stitching filter and the hue shift filter which are respectively adapted to correct the specific hue shift and stitching error created by the hardware components of this particular IAS.

According to embodiments, the image-artifact-generation logic is adapted to create image-capturing-device-specific artifacts. The method comprises providing a plurality of image acquisition systems; for each of the plurality of image acquisition systems: creating the first image-artifact-generation logic according to any one of the embodiments and examples described herein, whereby the first image-artifact-generation logic is specific to said image acquisition system; capturing, by said image acquisition system, a plurality of original images of a tissue sample; generating, for each of the plurality of original images a respective first artificially degraded image by applying the created image-acquisition-specific first image-artifact-generation logic on each of the original images; generating an image-acquisition-system-specific program logic configured for removing artifacts from digital tissue images captured by said image acquisition system, the generation comprising training an untrained version of a first machine-learning logic that encodes a first artifacts-removal logic on the original images and their respectively generated first degraded images; and returning the trained first machine-learning logic as the image-acquisition-system-specific program logic or as a component thereof.

Said features may be advantageous in particular in the context of image analysis in the biomedical domain, because often, image acquisition systems are highly complex systems whose components have been assembled specifically for the needs and demands of a particular research group or laboratory. For example, the components of a complex microscope system or slide scanner system may be obtained from different manufacturers, some components may be newer than others due to an exchange of dysfunctional or outdated parts, and the combination of components may be the result of an extensive and complex consultation between a representative of microscopy systems and the respective working group. In many cases, in particular in the context of biomedical research, the combination of components of a complex image acquisition system is unique. Hence, the automated creation of a IAS-specific artifact generation and removal algorithm may greatly increase the accuracy of all further image analysis steps performed on the images acquired by said IAS.

In a further aspect, the invention relates to a digital pathology image-correction method for digital images depicting a biological sample. The method comprises: receiving a digital image of the biological sample, the digital image comprising an artifact; applying the program logic generated in accordance with the method for generating the artifacts-removal-program logic described herein for embodiments of the invention on the received digital image for generating an artifact-corrected image; and returning the artifact-corrected image.

In a further aspect, the invention relates to a computer program comprising computer-interpretable instructions which, when executed by a processor, cause the processor to perform a method according to any one of the embodiments described herein. For example, the computer program can be stored on a digital volatile or non-volatile storage medium or can be stored in a cloud environment and be provided via a network to one or more clients.

In a further aspect, the invention relates to an image analysis system comprising a storage medium and a processor. The storage medium comprises a plurality of original images, each original image depicting a tissue. The processor is configured for generating a program logic configured for removing artifacts from digital tissue images. The processor is configured to perform a method comprising: generating, for each of the original images, a first artificially degraded image by applying a first image-artifact-generation logic on each of the original images, the first image-artifact-generation logic being configured for specifically generating a first type of artifact; The processor being in addition configured for generating the program logic, the generation comprising training an untrained version of a first machine-learning logic that encodes a first artifacts-removal logic on the original images and their respectively generated first degraded images; and returning the trained first machine-learning logic as the program logic or as a component thereof.

Any of the artifact-generation logics described herein can be applied on an original image for obtaining a single-fold degraded image. In addition, they can be applied on an already single-fold or multi-fold degraded image output by one or more other artifact-generation logic. In this case, the input image used by the artifact-generation logic is not an "original image" but a degraded version of an original image which can also be referred to as "intermediate degraded image" or "intermediate image".

An "original image" as used herein is an image that is acquired by an image capturing system or a derivative thereof. For example, an original image can be an RGB image or grey scale image obtained from a bright field microscope or can be a grey scale image obtained from a particular channel of a fluorescence microscope. It can also be a multi-channel image that is then decomposed into single-channel images. Preferably, an original image is an image having at least standard image quality, and preferably a good quality. Preferably, the original image should be basically free of artifacts, in particular be basically free of artifacts which shall be introduced later by applying an artifact-generation-logic on the original image.

An "autoencoder", "autoassociator" or "Diabolo network" as used herein is a network architecture for which the input and output data sizes are equal. For example, the input image may be an RGB image of a dimension of 100×100 pixels and the output generated by the autoencoder for this image can be also an RGB image of a size of 100×100 pixels. An autoencoder is adapted to learn a function from $R^N => R^N$ where N is the number of pixels in the input and output images, respectively. The autoencoder can be an artificial neural network used for unsupervised learning. An autoencoder is configured to learn a representation (encoding) for a set of data, typically for the purpose of dimensionality reduction. In particular, an autoencoder can be configured for learning generative models of data by learning an approximation to identity function using backpropagation. Architecturally, the simplest form of an autoencoder is a feedforward, non-recurrent neural network very similar to the multilayer perceptron (MLP)—having an input layer, an output layer and one or more hidden layers connecting them—, but with the output layer having the same number of nodes as the input layer, and with the purpose of reconstructing its own inputs (instead of predicting the target value Y given inputs X). Therefore, autoencoders are unsupervised learning models. An autoencoder can be, in particular, a denoising autoencoder.

An "image artifact" or "artifact" as used herein is an optical feature or pattern that appears in an image of a tissue, in particular of a stained tissue, and is the result of an error or undesired event that occurred during the preparation, fixation or staining of a tissue sample or during image acquisition of a digital image of the tissue sample.

A "staining artifact" as used herein is an artifact which is caused by an error or undesired event during the sample preparation, fixation or staining. A staining artifact can result from a number of causes including improper fixation, improper type of fixative, poor dehydration, improper reagents, poor microtome sectioning, improper type or concentration of stain, improper staining temperature, improper staining duration, improper pH of the staining solution and the like.

A "scanning artifact" as used herein is an artifact which is caused by an error or undesired event during the image capturing process.

A "tissue-fold artifact" as used herein is an artifact that results from an erroneous generation of a tissue sample or from an error that occurred while mounting the tissue sample on a slide, whereby the depicted tissue comprises one or more folds. For example, in case a tissue is insufficiently dehydrated prior to clearing and infiltration with paraffin wax, the tissue may not be sectioned correctly on the microtome, leading to tearing and holes in the sections. A "tissue fold artifact" can also be produced when tissue adheres to the under surface of the blade. This type of artifact is commonly observed when the blade used for cutting the tissue is dull and/or when the tissue is fatty tissue.

A "line-artifact" as used herein is an artifact that has the shape of a curved or straight line or comprises sections having the shape of a curved or straight line. For example, air bubbles in the tissue sample (in particular the outline of the bubbles), hair and fibers of cloth or of other origin often have the form of a line, e.g. the form of a circular line in the case of air bubbles. Bubbles under the coverslip may form when the medium used for mounting the tissue sample on a slide is too thin, because, as the medium dries, air is pulled in under the coverslip. Contamination of clearing agents or coverslipping media may also produce a bubbled appearance under the microscope.

An "anthracotic pigment artifact" as used herein is an image region that erroneously appears to be strongly stained because of minute carbon particles deposited in lung tissue that give the tissue the black coloration seen in anthracosis.

A "non-specific staining artifact" as used herein is an image artifact created by staining dyes that were not washed out during the staining process. Thus, a non-specific staining artifact represents a tissue-region or non-tissue region that comprises a significant amount of stain that was supposed to selectively stain specific tissue regions but was observed to stain additional regions inside of or outside of the tissue. The remaining dyes create patches of various sizes with a specific color of the dye which typically do not comprise any tissue-specific patterns or intensity gradients. Some forms of the "non-specific staining artifacts" may also be referred to as "residual staining artifacts".

A "hue shift artifact" as used herein is an image artifact in which the intensity values of all pixels of an image or of some regions of an image deviate from the expected pixel intensities. For example, a hue shift artifact can be generated by some erroneous hardware of an IAS that comprises a sensor which is more sensitive to light on the left side than on its right side. Such reproducible, systematic errors of the hardware IAS may be compensated by loftware logic according to embodiments of the invention. A "Point spread function (PSF)" as used herein is a function that describes the response of an imaging system, e.g. a microscope, to a point source or point object.

A "filter" as used herein is a function of a program logic that specifies one or more image processing operations. For example, a filter may comprise a function that increases or decreases the pixel intensity values in dependence on the x- and y coordinate of the pixel in an input image.

A "logic" as used herein is a set of machine-interpretable instructions that, when executed by a processor, causes the processor to perform at least one function, e.g. the removal of a particular artifact from an input image.

A "digital pathology method" as used herein is a method to be used in the field of digital pathology. Digital pathology is an image-based information environment which is enabled by computer technology that allows for the management of information generated from a digital slide. Digital pathology is enabled in part by virtual microscopy, which is the practice of converting glass slides into digital slides that can be viewed, managed, and analyzed on a computer monitor. The field of digital pathology is currently regarded as one of the most promising avenues of diagnostic medicine in order to achieve even better, faster and cheaper diagnosis, prognosis and prediction of cancer and other important diseases.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These and other aspects will now be described by way of example with reference to the accompanying drawings, of which:

In the following embodiments of the invention are explained in greater detail, by way of example only, making reference to the drawings in which:

FIG. 1 is a flowchart of a method of generating an artifacts-removal logic according to one exemplary embodiment of the invention. The method can be performed, for example, by an image processing system according to a further embodiment of the invention that is depicted in FIG. 2. In the following, the method of FIG. 1 will be described by making reference to FIG. 2.

FIG. 2 shows an image analysis system 200. The system comprises a data processing system 202 with one or more processors 228, e.g. a standard desktop computer system, a notebook, a tablet computer or a server computer system. The image analysis system 200 comprises or is operatively coupled to an image acquisition system 204, e.g. a brightfield or fluorescence microscope or a slide scanner. In the image acquisition system comprises a camera 212. The data processing system 202 comprises an interface for receiving the digital images of tissue slides captured by camera 212.

For example, the interface can be a network connection, an USB stick, a CD-ROM drive or the like. The processing system 202 comprises a non-volatile storage medium 240 which stores a plurality of original images 208. The original images can be RGB images or grayscale images as generated by the camera 212 are can be preprocessed images whose resolution, contrast, color space or other feature may differ from the image that was originally captured by the camera. The following, it will be assumed that the original images 208 are rgb images captured by a camera of a brightfield microscope.

Figure 1:
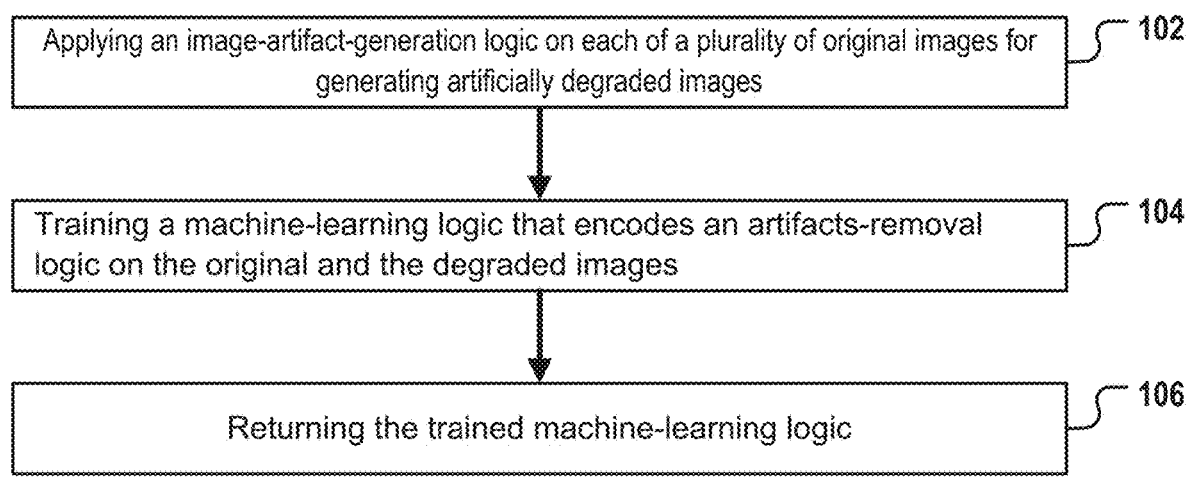
FIG. 1 is a flowchart of a method of generating an artifacts-removal logic.
Figure 2:
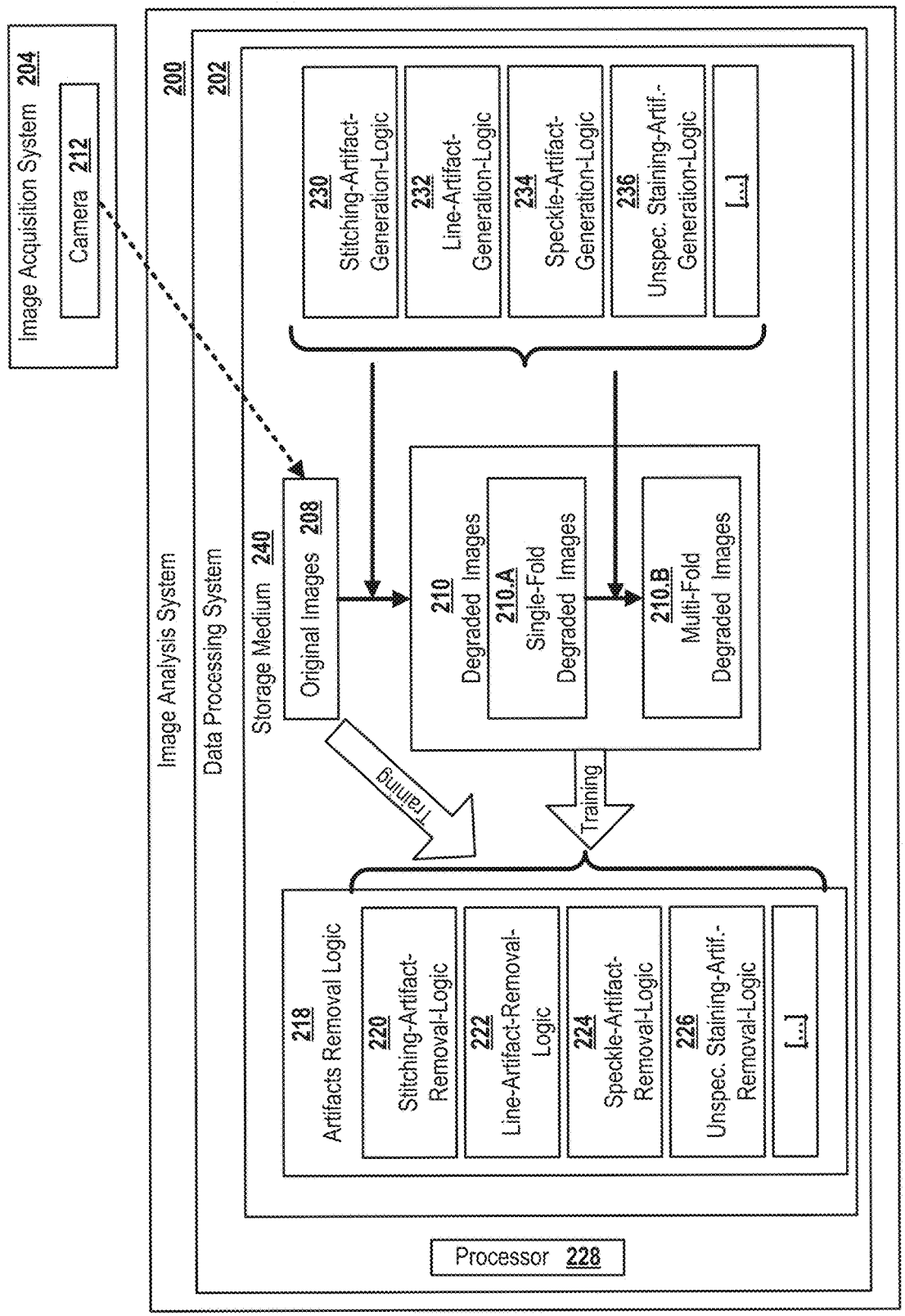
FIG. 2 is a block diagram of an image analysis system.

The storage medium may further comprise a plurality of artifact generation logics 230-236 which can respectively be implemented as standalone software applications. Alternatively, the artifact generation logics 230-236 are implemented as components of a single software application. Preferably, a user is enabled to specifically select one or more of the artifact generation logics for generating degraded images comprising a single specific type of artifact or comprising two or more artifacts which were generated according to one or more predefined chronological sequences of artifact generation. FIG. 2 shows only a subset of the artifact generation logics described herein: a stitching-artifact-generation-logic 230, a line-artifact-generation-logic 232, a speckle-artifact-generation-logic 234, and an unspecific-staining-artifact-generation-logic 236. Further artifact generation logics or a different subset of artifact generation logics described herein may be comprised in the data processing systems of other embodiments. Depending on the embodiment and/or on the type of artifact, the respective artifact-generation-logic can be specified manually or automatically based on a machine learning approach on tissue images comprising the "real" artifact. Depending on the embodiment and/or the type of artifact, the artifact-generation-logic can be in specified once for a particular type of artifact, or can be specified once for a particular type of image acquisition system 204, or can be specified once for an individual image acquisition system. For example, the stitching-artifact-generation-logic 230 can be obtained specifically for a particular type of microscope or even for an individual microscope system by acquiring calibration images via a particular image acquisition system and fitting a square filter or other mathematical function such that the filter faithfully reproduces the stitching pattern observed within the calibration images (not shown).

The larger the number of different artifact-generation-logics stored in the storage medium 240, the larger the types of artifacts that can be generated automatically, the larger the number of combinations of artifacts of different types and the larger the training data set that can be generated automatically from the original images 208. Preferably, the original images 208 are high quality images which are basically free of image artifacts, or at least are basically free of image artifacts of an artifact type that shall be artificially generated by one of the artifact-generation-logics in the following steps.

In a first step 102, the image analysis system applies one of the image-artifact-generation-logics 230, 232, 234, 236 on each of the original images 208. Thereby, for each of the original images, an artificially degraded image is generated. For example, if the stitching-artifact-generation-logic 230 is applied on an original image, the resulting degraded image will show a stitching pattern that is added, superimposed, multiplied or otherwise combined by the artifact-generation-logic 230 with the pixels of the original image. Depending on the embodiment, the generation of a degraded version of an originally received image can be performed right after or during the image acquisition by an image acquisition system or can be performed many days after the images were acquired.

After having created, for each of the original images, a respective degraded image by applying one of the artifact-generation-logics 230-236, a training data set is obtained that comprises the original images 208 and the respectively (single-fold) degraded images 210.A.

Then, an artifacts removal logic 218 is generated. The generation of the artifacts-removal-logic 218 comprises a step 104 of training a machine learning logic that encodes an artifacts-removal logic on the original images 208 and the degraded images 210 and returning, in step 106, the trained machine-learning logic 218.

For example, in case the training data set consists of original images and degraded images generated by the stitching-artifact-generation logics 230 (and is free of images comprising any other artifact type), the generated artifacts removal logic 218 will basically be configured for selectively removing, via the stitching-artifact-removal-logic 220, stitching artifacts of a particular camera or camera type. The artifacts removal logic will not be able to remove line artifacts, speckle artifacts or the like. In case the training data set 210 in addition comprises degraded images generated by other artifact generation logics 232-236, the artifacts removal logic 218 will be trained on an information-enriched training data set and will be adapted to remove artifacts of multiple different types. Preferably, the training data set that is used for generating the respective artifact-removal logics 220-226 comprises meta-data being descriptive of the particular artifact generation logic that generated a particular degraded image from a particular one of the original images 208.

In some embodiments, the artifacts-removal logic 218 is configured to solely and selectively remove artifacts of a particular, single artifact type from an image. According to the embodiment depicted in FIG. 2, the artifacts removal logic 218 comprises a plurality of functionalities 220, 222, 224, 226 which are respectively trained and adopted to remove image artifacts of a particular type from an image.

According to some embodiments, the image analysis system 200 is configured to generate, for each of the original images and for each of the artifact-generation-logics 230-236, a respective (single-fold) degraded image. The original images and the single-fold degraded images related to a particular artifact type are used for training an artifact-type specific artifacts removal logic. In some embodiments, the artifacts removal logic 218 is a single machine learning architecture which is trained on a training data set comprising degraded images relating to many different artifact types and which comprises sub-functionalities (which may act as black boxes) respectively having learned to remove artifacts of a particular artifact type.

In other embodiments, each of the artifact-removal logics 220-226 is generated by training an untrained version of a machine learning logic on training data selectively comprising image artifacts of a particular type. The generated, trained machine learning logic 220-226 are later combined into a single software application which allows the user to remove artifacts of multiple different types from an input image.

According to preferred embodiments, the artifact-generation-logics 230-236 are not only applied once on the original images for generating single-fold degraded images 210.A. Rather, the image analysis system can be configured for applying the artifact-generation-logics sequentially, whereby the degraded image output by any one of the artifact-generation-logics in the sequence is used as input by the following artifact generation logics. For example, the stitching-artifact-generation-logic 230 can read an original image 208 from the storage medium 240 and output a first intermediate image comprising a stitching artifact. The first intermediate image is then used as input by the line-artifact-generation-logic 232 for generating a second intermediate image which again is used as input for a further artifact-generation-logic.

In some embodiments, a user may specify the sequence of the artifact-generation-logics applied for generating multi-forwards degraded images 210.B manually. Preferably, the user will specify the sequence of artifact generation operations such that the sequence represents the "real" chronological sequence of artifact generation that is expected to occurred during the staining and image acquisition. In other embodiments, the image analysis system 200 automatically determines, for a given set or subset of artifact-generation-logics 230-236, many or all of the combinatorially possible sequences of applying the way a artifact-generation-logics. Then, a training data set is generated that comprises the original images 208 and multi-fold degraded images 210.B, whereby at least some of the multi-fold degraded images have been created by the same set of artifact-generation-logics but based on different chronological sequences. This may be beneficial, because the chronological sequence of artifact generation may differ from case to case and a training data set that comprises many different chronological sequences of applying artifact types may allow the artifacts-removal logic 218 to "learn" many different sequences of removing artifacts from images. This may be beneficial, because depending on the particular staining protocol, the staining dye, the stained tissue, and in the used image acquisition system, different artifact types in different chronological sequences may be observed and the "real/most probable" sequence of artifact generation may not be known or may differ from case to case. By automatically generating highly information enriched training data set, embodiments of the invention may allow generating and artifacts removal logic that is able to accurately remove many different types of artifacts in accordance with many different chronological artifacts removal schemes from digital pathology images.

According to embodiments, each of the artifacts removal logics 220-226 is implemented as a fully convolutional neural network. According to other embodiments, the combined artifacts removal logic 218 is implemented as a single fully convolutional neural network.

In some embodiments, the machine-learning-logic that is employed for learning the artifacts removal logic for individual or all artifact types is a neural network having a network architecture that is described, for example in Long, Jonathan, Evan Shelhamer, and Trevor Darrell. "Fully convolutional networks for semantic segmentation." Proceedings of the IEEE Conference on Computer Vision and Pattern Recognition, 2015. Preferably, the network is a fully convolutional network trained end-to-end and pixels-to-pixels. The network can be generated by adapting contemporary classification networks such as AlexNet, the VGG net, and GoogLeNet into fully convolutional networks.

The fully convolutional network is adapted for learning how to remove an artifact or a particular type by applying a model-based artifacts-removal algorithm on a degraded version of an image for generating an automatically reconstructed image, comparing the original image with the reconstructed image and, in case the difference is too high (e.g. exceeds a threshold), modifying the model such that the difference between the reconstructed image and the original image is minimized. Thus, the machine learning logic "learns" a model that is capable of removing artifacts of a particular type from an image.

In some preferred embodiments, the machine learning logic 218, 220, 222, 224, 226 is implemented as a "denoising autoencoder" with at least one type of noise artifact model corresponding to the noise artifact types described herein. As a result, the trained machine-learning logic ("trained denoising encoder") is adapted to remove artifacts of this particular type from an input image. The network architecture can consist of a Deep Convolutional Neural Network setup with encoder and decoder mechanisms e.g. FCN-8s (in Long, Jonathan, Evan Shelhamer, and Trevor Darrell. "Fully convolutional networks for semantic segmentation." Proceedings of the IEEE Conference on Computer Vision and Pattern Recognition, 2015), or Lovedeep Gondara, Simon Fraser University, "Medical image denoising using convolutional denoising autoencoders, ArXiv preprint arXiv: 1608.04667, 2016. Another example for a suitable network architecture is presented in Unet (Ronneberger Olaf et al.: "U-Net: Convolutional Networks for Biomedical Image Segmentation", chapter in "Medical Image Computing and Computer-Assisted Intervention", MICCAI 2015: 18th International Conference, Munich, Germany, Oct. 5-9, 2015, Proceedings, Part III", Springer International Publishing", ISBN="978-3-319-24574-4".

The training of the machine-learning logic 218, 220-226 comprises inputting each artificially degraded image together with the respective original non-degraded image to enable the autoencoder to learn to recreate the original image from the "degraded" image.

The artifact generation logics 230-236 are specified manually or are generated automatically or semi-automatically based on a machine learning approach. For example, the stitching-artifact-generation-logic can be obtained by automatically learning a square filter from one or more images taken by a camera of a particular IAS of an empty slide. To the contrary, the salt-and-pepper noise generation function can be specified explicitly by a programmer.

Figure 3:
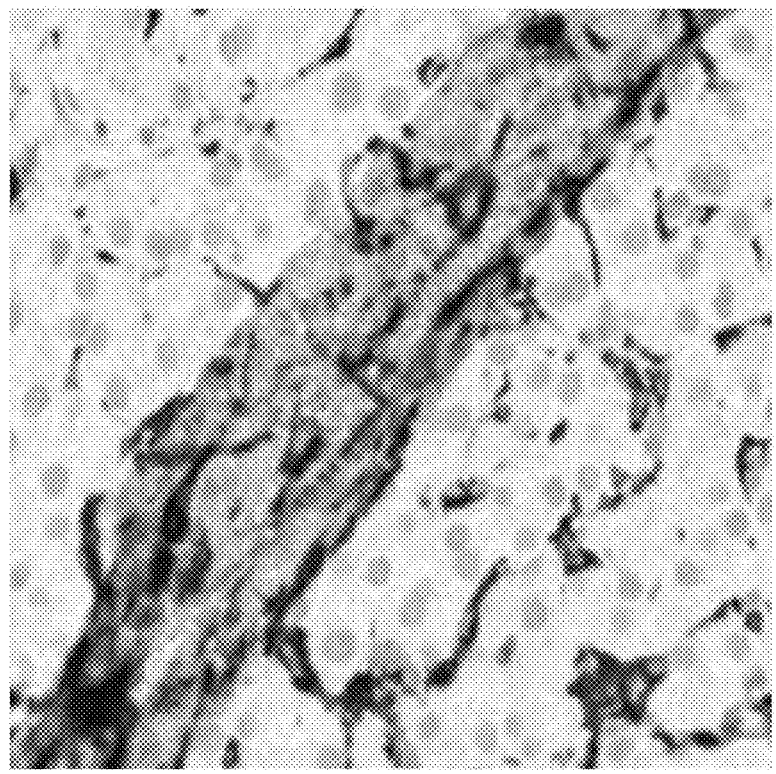
FIG. 3 is a digital tissue image with a tissue fold artifact.

FIG. 3 is a digital tissue image depicting a "real" tissue fold artifact. This type of image artifact is often the result of the use of blunt knifes during tissue cutting or of handling errors during the slide mounting. According to some embodiments of the invention, a tissue-forward-artifact-generation logic is provided which is configured to automatically add an artificial tissue-fold artifact on an input image for generating a degraded version of the image. The generation of the tissue-fold artifact comprises virtually cutting the original image into image parts, overlaying the image parts such that the parts overlay along the cutting line, e.g. for an overlay margin of about 3 to 10 pixels. The resulting degraded image looks very similar to an image comprising a "real" tissue fold artifact.

Figure 4:
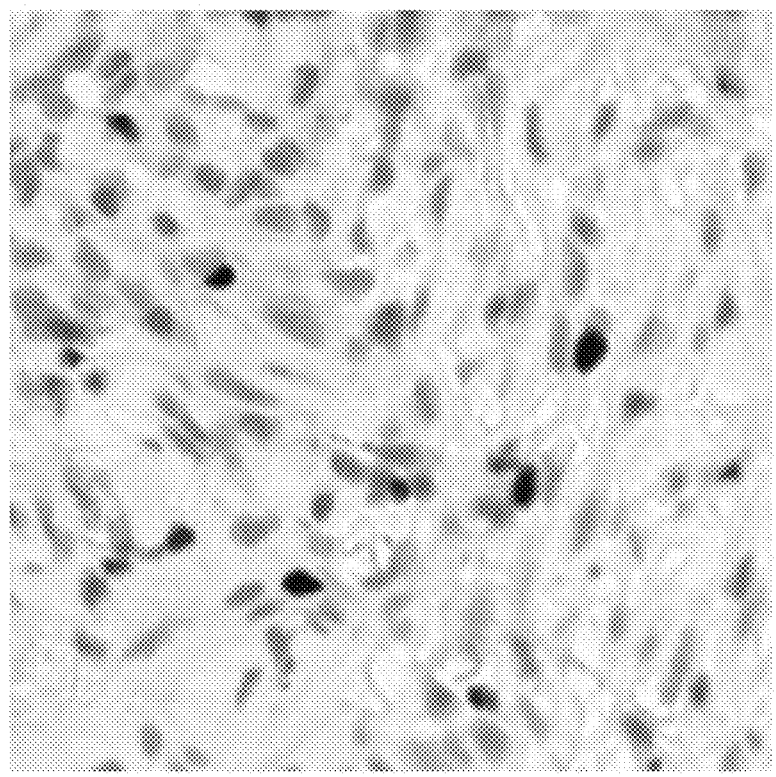
FIG. 4 is a digital tissue image with a speckle noise artifact.

FIG. 4 is a digital tissue image with a "real" speckle noise artifact. A speckle noise is often caused by dust in the camera objects or on the cover slide of a tissue slide. Speckle noise can also be generated by bad pixels in the sensor cells of a camera. According to some embodiments, a speckle-artifact-generation-logic 234 implements a salt-and-pepper-noise generation function. This function is capable of faithfully reproducing the speckle noise often observed in digital pathology images. Preferably, the function randomizes the radii of the speckles.

Figure 5:
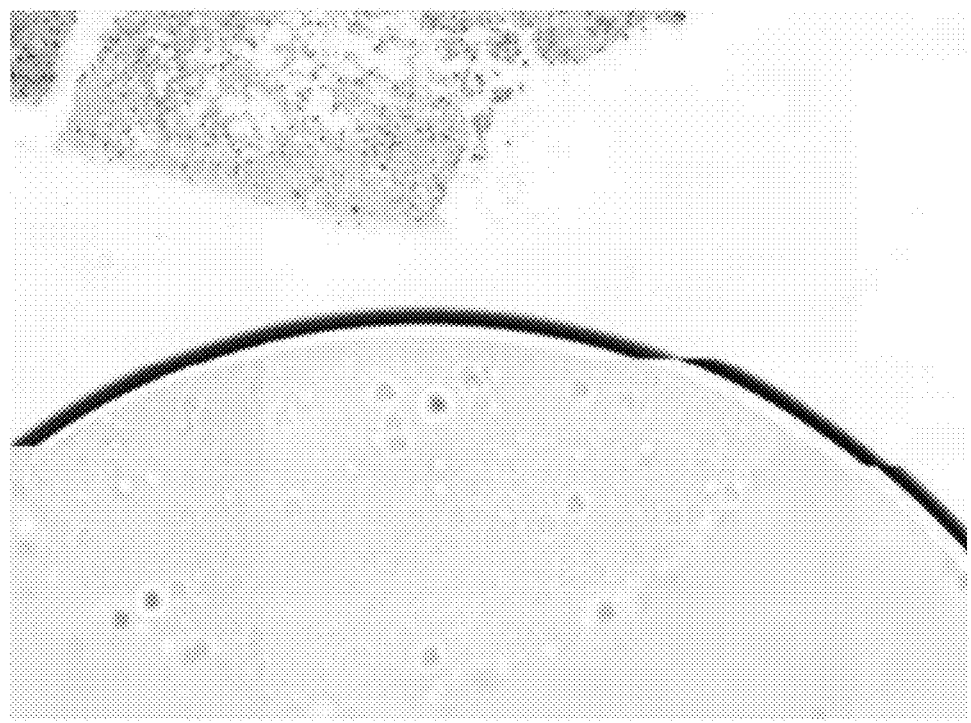
FIG. 5 is a digital tissue image with a line artifact.

FIG. 5 is a digital tissue image with a line artifact caused by an air bubble. According to some embodiments, a line-artifact-generation logic 232 is configured to randomly select polynomial parameter of different orders, to generate a black line in accordance with that parameters and with the typical thickness of air bubble margins in a digital image.

Figure 6:
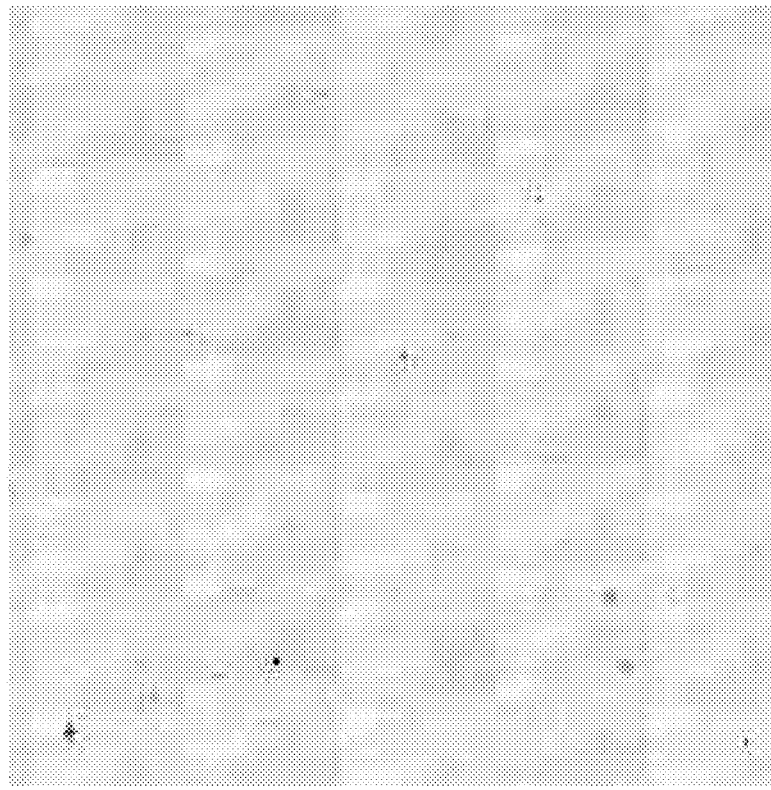
FIG. 6 is a digital tissue image with a stitching artifact.

FIG. 6 is a digital tissue image with a stitching artifact. A "stitching artifact" or "stitching-noise-artifact" is an image artifact generated by the optics or mechanics of the image acquisition system 204, whereby the image acquisition system can in particular be a slide scanner. According to embodiments, a stitching-artifact-generation-logic 230 implements a square filter that is applied on any input image received by the program logic 230, thereby generating and returning a degraded image comprising a simulated stitching artifact. Preferably, the square filter is obtained empirically by analyzing the image of an empty slide obtained by a particular image acquisition system. The square filter is automatically or manually fitted such that it faithfully reproduces the observed stitching pattern of the image acquisition system. Then, in the stitching-artifacts-generation-logics 230 automatically generates, for each of a plurality of original images, a respective degraded image comprising the simulated stitching artifact of a particular image acquisition system. The original images and the degraded images are used as training data set for training and stitching-artifact-removal logic 220 that is capable of selectively removing the stitching artifact generated by a particular image acquisition system or type of image acquisition system.

Figure 7:
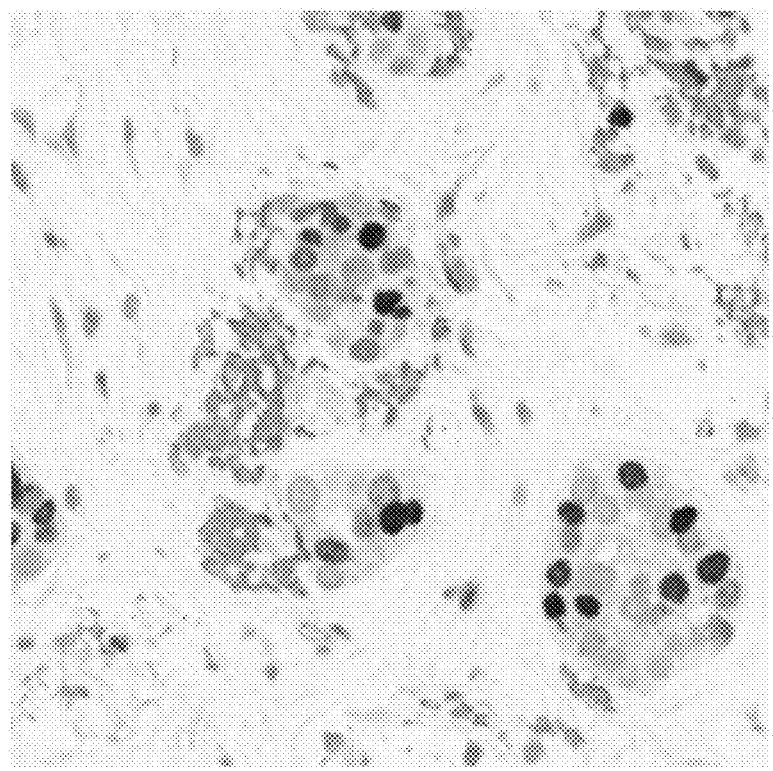
FIG. 7 is a digital tissue image with a non-specific staining artifact.

FIG. 7 is a digital tissue image with a "real" non-specific staining artifact. Non-specific staining artifacts can be simulated, e.g. by a program logic 236, by applying a color-specific salt-and-pepper speckle noise generation function, whereby the color of this function corresponds to the type of stain whose unspecific staining artifacts shall be simulated and removed. For example, the program logic 226 of the image acquisition system is generated based on a machine learning approach from a training data sets comprising original images 208 and artificially degraded images generated by program logic 236. The program logic 226 is configured to selectively remove unspecific staining artifacts of a particular stain from a digital pathology image.

Figure 8:
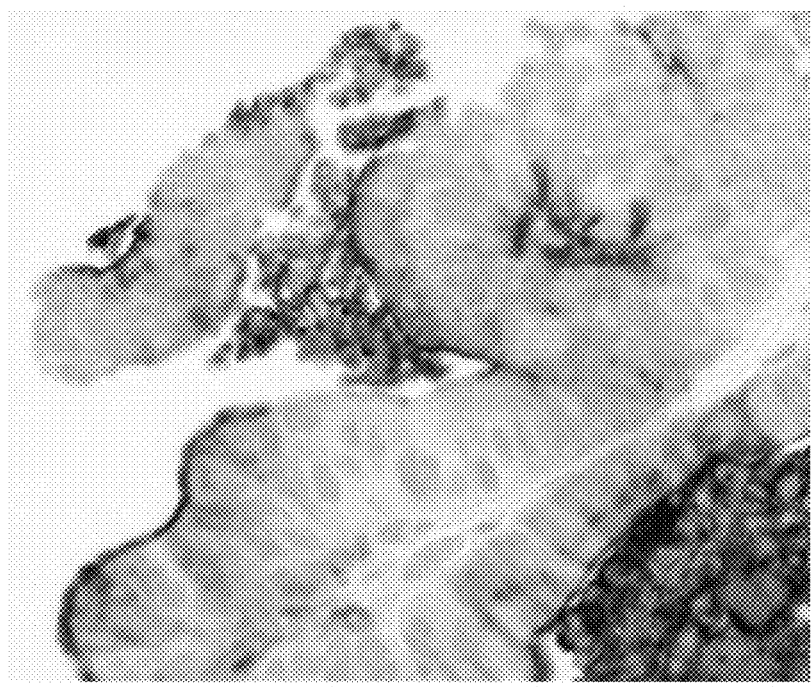
FIG. 8 is a digital tissue image with a bad-focus artifact.

FIG. 8 is a digital tissue image with a "real" bad-focus artifact that is the result of a microscope focus loss. According to embodiments, degraded images comprising bad-focus noise can be automatically created by modeling a point spread function (PSF) or a Gaussian approximation of a PSF for a particular image acquisition system, e.g. for a particular microscope or microscope type.

Figure 9:
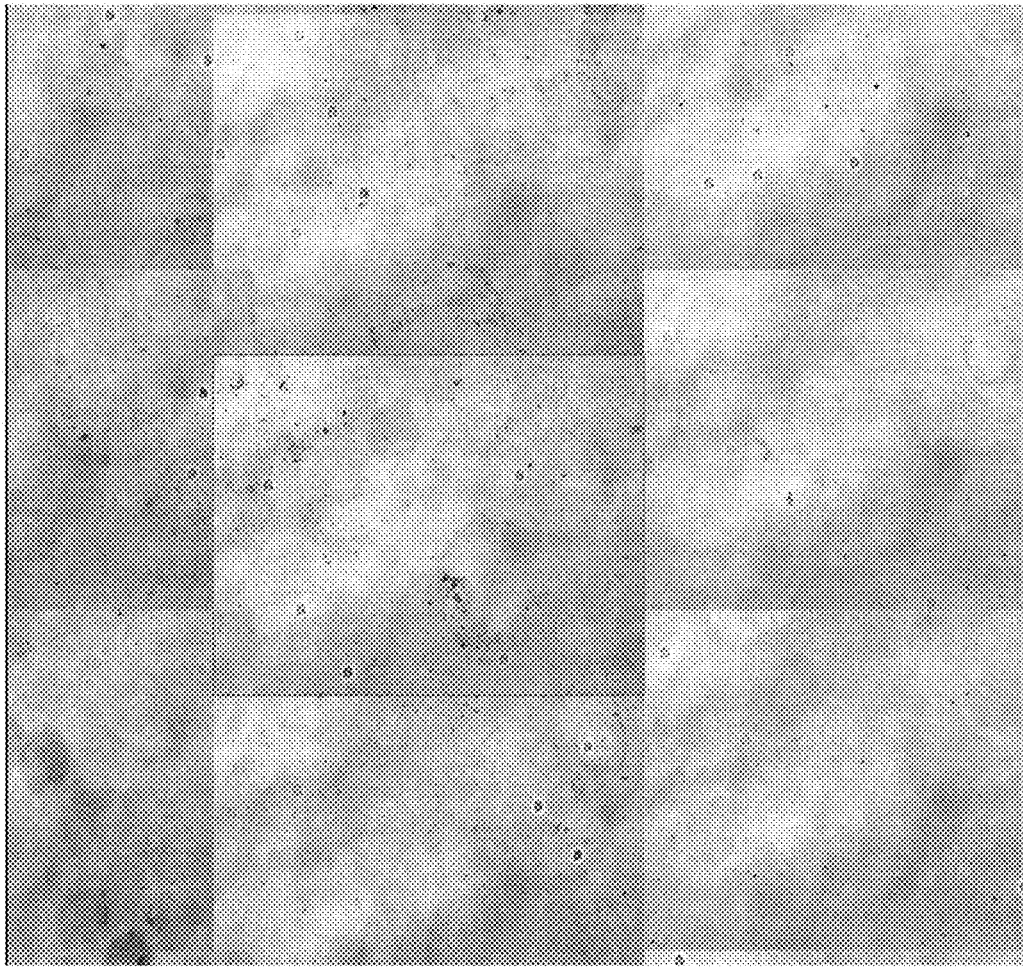
FIG. 9 is a digital tissue image with a stitching artifact created with image acquisition system specific parameters.
Figure 10:
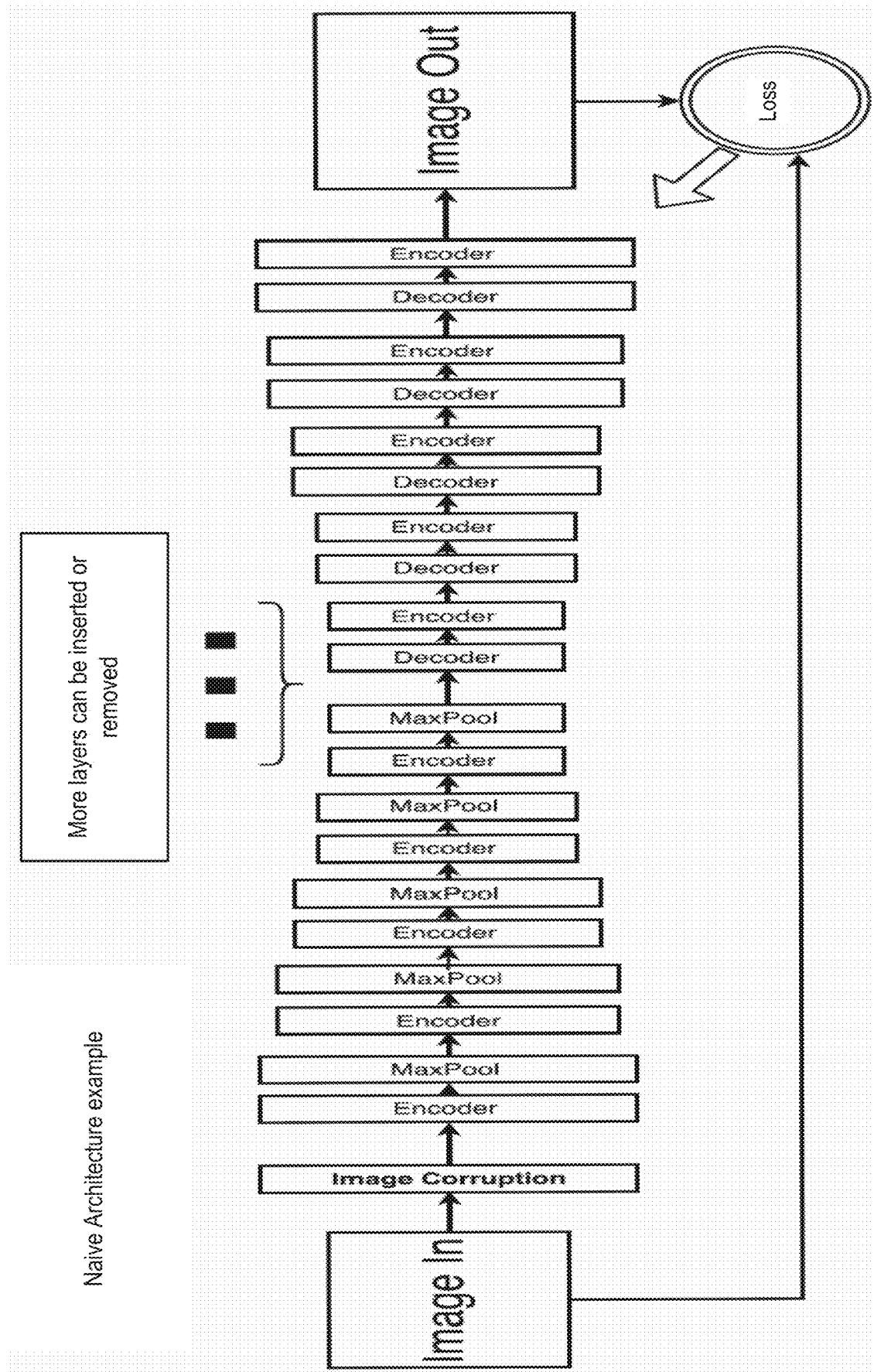
FIG. 10 is a block diagram of a "naïve" Neural Network architecture.

FIG. 9 depicts a digital tissue image with a stitching artifact created with image acquisition system specific parameters;

FIG. 10 is a block diagram of a "naïve" Neural Network architecture used as a machine learning logic according to embodiments of the invention. The depicted network architecture can be trained to learn the generation of an artifact of a single artifact type. Alternatively, the network architecture can be trained to generate a predefined sequence of artifacts of different types. In addition, or alternatively, the network architecture depicted in this figure can be trained to remove an artifact of a particular artifact type or to remove multiple artifacts of different types in a predefined sequence. More layers can be inserted or removed to increase or decrease the complexity of the network. By adding and removing layers from the network and by testing the accuracy of the trained network on a reference data set, a network architecture with an optimum number of layers can be determined experimentally.

Figure 11:
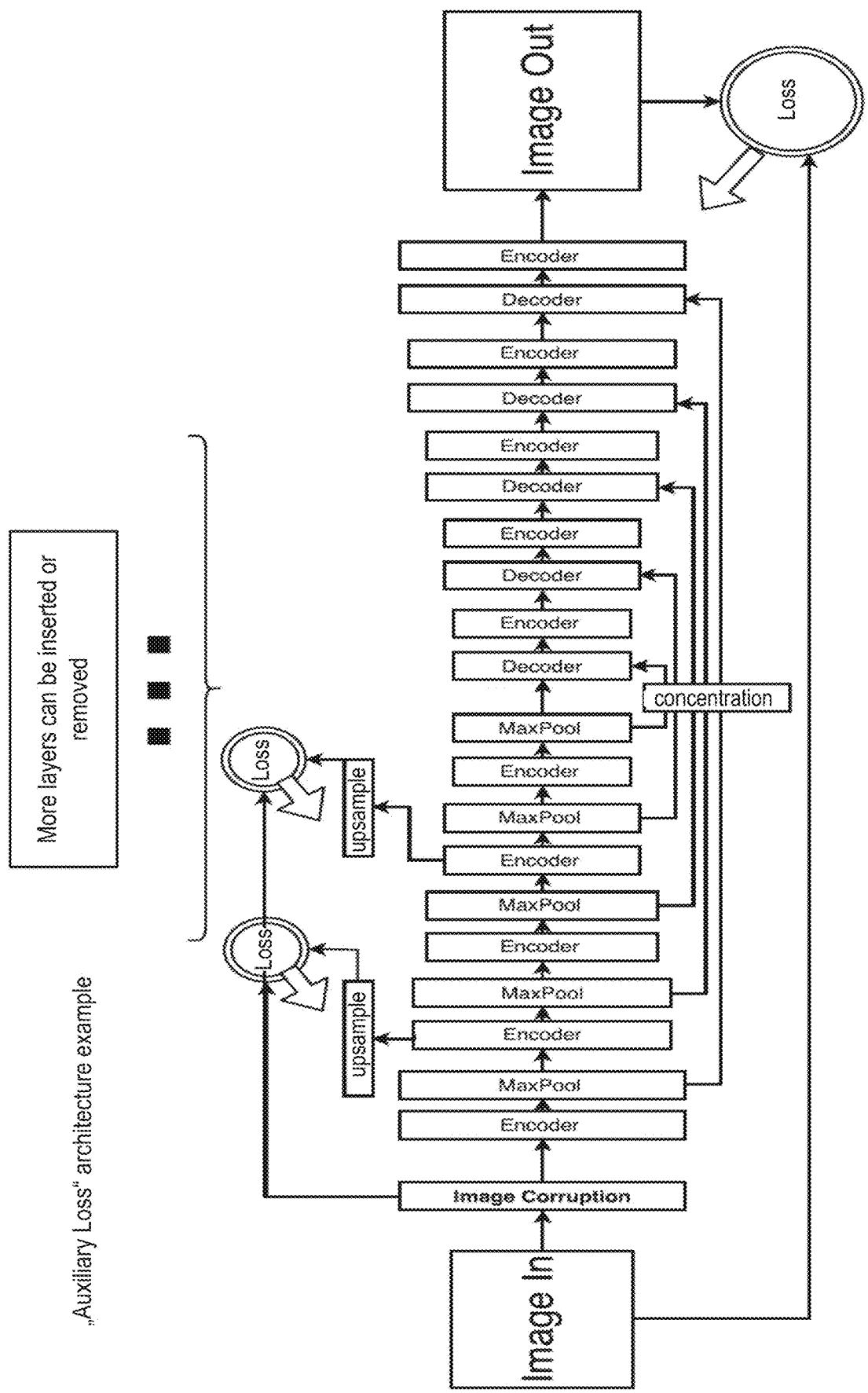
FIG. 11 is a block diagram of an "auxiliary loss" Neural Network architecture.

FIG. 11 is a block diagram of an "auxiliary loss" Neural Network architecture used as machine learning logic in some other embodiments of the invention. The network architecture depicted in FIG. 11 can basically be used in the same manner and for the same purposes as the architecture depicted in FIG. 10.

Both the "naïve network" and the "auxiliary loss" network architecture can be used as the program logic that learns to create and/or remove a particular artifact type. Both the "naïve network" and the "auxiliary loss" network architecture can be used as the program logic that learns to create and/or remove sequences of artifacts. The "auxiliary loss" network, however, allows a tighter control of the training process, because sub-sets of layers in the network have assigned a "teacher" on their own which may allow to achieve a training of said sub-set of layers to generate or remove a particular artifact type.

Figure 12C:
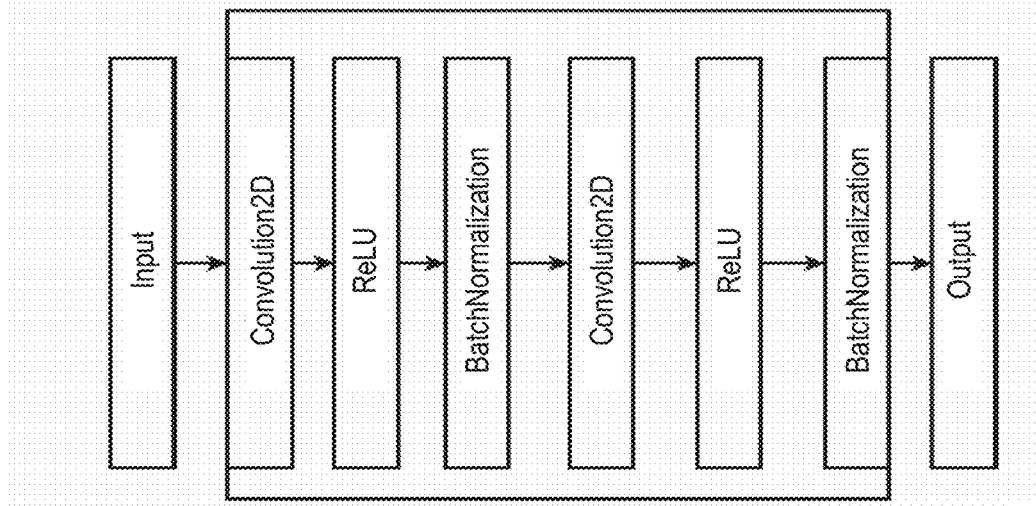
FIG. 12*c* is a block diagram of a Basic Decoder Unit.
Figure 12B:
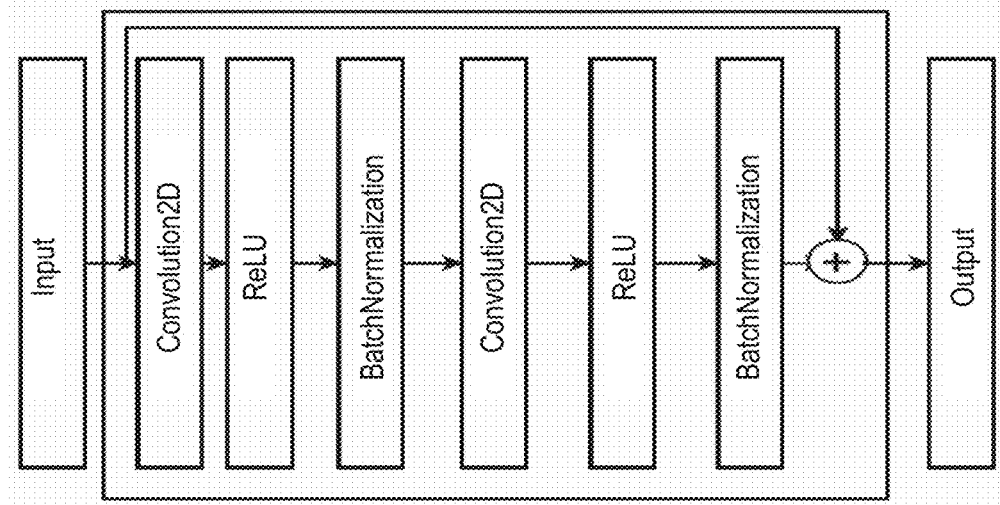
FIG. 12*b* is a block diagram of a Residual Encoder Unit.
Figure 12A:
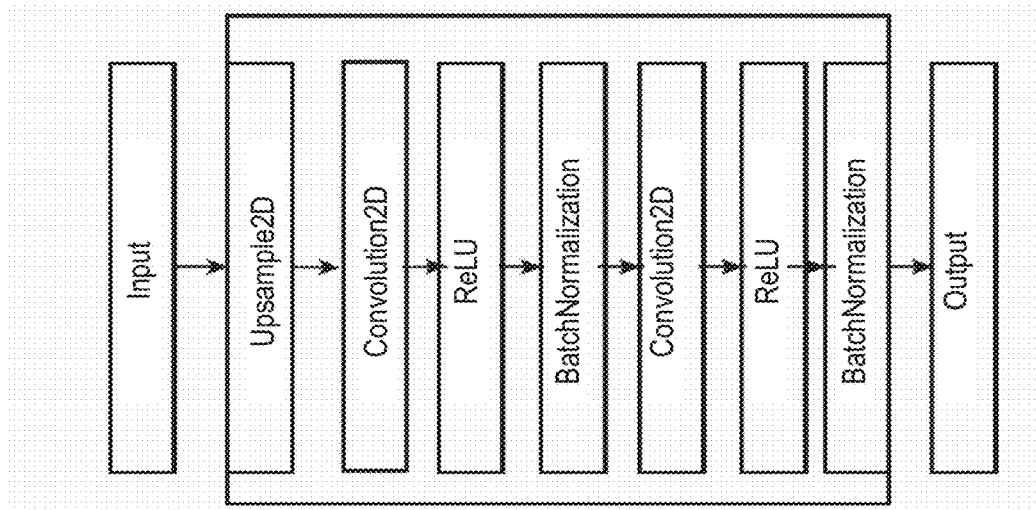
FIG. 12*a* is a block diagram of a Basic encoder Unit.

FIG. 12a is a block diagram of a basic encoder unit as used, for example, in a neural network depicted in FIG. 10 or 11. The basic encoder unit forms a sequence of normalization layers wherein a batch normalization layer precedes the rectification layer (rectified linear unit—ReLU) layer.

FIG. 12b is a block diagram of a Residual Encoder Unit as used, for example, in a neural network depicted in FIG. 10 or 11. The basic encoder unit forms a sequence of normalization layers wherein the ReLU layers precede the batch normalization layer.

FIG. 12c is a block diagram of a Basic Decoder Unit that has a similar architecture like the unit depicted in FIG. 12a. In addition, it comprises an unsampling layer.

Each Layer depicted in FIGS. 12a-12c has a function in a network, e.g. in one of the networks depicted in FIGS. 10 and 11. For instance, convolotion2d applies 2d convolutional filters, batch normalization normalizes the gradients during training, upsampling makes the image bigger, and pooling downsamples the image. The layers can respectively comprise parameters whose values are learned (optimized) during the training phase.

The invention claimed is:

1. A method for providing program logic adapted to remove artifacts from digital tissue images, the method comprising:
  creating first image-artifact-generation logic, the first image-artifact-generation logic being configured for specifically generating a first type of artifact, the first image-artifact-generation logic being an image-acquisition-system-specific image-artifact-generation logic, the image-acquisition-system-specific image-artifact-generation logic being a stitching-artifact-generation-logic, the creating the stitching-artifact-generation-logic including,
    taking, by an image acquisition system that is used for capturing a plurality of original images, a digital image of an empty slide,
    analyzing the digital image of the empty slide for automatically creating a square filter that is configured to simulate a stitching artifact generated by the image acquisition system, and
    creating the first image-artifact-generation logic by integrating the square filter into a machine-executable code;
  generating, for each of a plurality of original images respectively depicting a tissue sample, a first artificially degraded image by applying the first image-artifact-generation logic on each of the original images; and
  generating a program logic configured for removing artifacts from digital tissue images, the generating the program logic including training an untrained version of a first machine-learning logic that encodes a first artifacts-removal logic on the original images and their respectively generated first degraded images, and returning the trained first machine-learning logic as the program logic or as a component thereof.

2. The method of claim 1, wherein when the program logic is applied on a received digital image, the square filter is applied to the received digital image, the applying the square filter on the received digital image including,
dividing the received digital image to squares of a width and height equal to an observed stitching artifact width and height, and
multiplying intensity values of the pixels of the stitching artifact with pixel intensities of each the squares of the received digital image onto which the square filter is mapped and applied to generate a pattern of degraded squares that simulate the stitching artifact.

3. The method of claim 1, further comprising:
generating, for each of the original images, a second artificially degraded image by applying a second image-artifact-generation logic on each of the original images, the second image-artifact-generation logic being configured for specifically generating a second type of artifact, and wherein
the generating of the program logic configured for removing artifacts further includes:
training an untrained version of a second machine-learning logic that encodes a second artifacts-removal logic on the original images and their respectively generated second degraded images; and
combining the trained first machine-learning logic with the trained second machine-learning logic for providing the program logic, the program logic being configured for removing artifacts of at least the first and the second artifact type.

4. The method of claim 3, wherein the second image-artifact-generation logic is A) an image-acquisition-system-specific image-artifact-generation logic or B) a tissue-staining-artifact-generation logic, the second image artifact generation logic being different from the first image-artifact-generation logic.

5. The method of claim 1, wherein the program logic is configured for removing artifacts of multiple different types, and the method further comprising:
providing, for each of the different artifact types, a respective image-artifact-generation logic configured for specifically generating a respective one of the different artifact types; and
applying, according to a first sequence, the different image-artifact-generation logics on each of the original images, whereby the image-artifact-generation logic at the first position within the first sequence takes each of the original images as input and wherein the degraded image output by said image-artifact-generation logic and any image-artifact-generation logic at a subsequent position within the first sequence is used as input image by the next one of the different image-artifact-generation logics in the first sequence, thereby generating, for each of the original images, a first multi-fold degraded image, wherein
the generating of the program logic further includes:
training a machine-learning logic that encodes a multi-step-artifacts-removal logic, the training being performed on at least the original images and their respectively generated first multi-fold degraded images; and
using said trained multi-artifact-machine-learning logic as the program logic or as part of the program logic, the program logic being configured for sequentially removing artifacts of each of the multiple types of artifacts.

6. The method of claim 5, further comprising:
applying, according to at least a second sequence, different image-artifact-generation logics on the original images, whereby the image-artifact-generation logic at the first position within in the second sequence takes each of the original images as input and wherein the degraded image output by said image-artifact-generation logic and any image-artifact-generation logic at a subsequent position within the second sequence is used as input image by the next one of the different image-artifact-generation logics in the second sequence, thereby generating, for each of the original images, a second multi-fold degraded image, wherein
the training of the untrained version of the machine-learning logic is performed on at least the original images and their respectively generated first and second multi-fold degraded images.

7. The method of claim 1, further comprising:
automatically creating a plurality of sequences of the different image-artifact-generation logics, each of the plurality of sequences comprising different image-artifact-generation logics at a first, a second and at least a third position by permutating the positions of the image-artifact-generation logics within the respective sequence; and
applying, for each of the plurality of sequences, the image-artifact-generation logics of said sequence on the original images, whereby the image-artifact-generation logic at the first position within in said sequence takes each of the original images as input and wherein the degraded image output by said image-artifact-generation logic and any image-artifact-generation logic at a subsequent position in said sequence is used as input image by the next one of the different image-artifact-generation logics in said sequence, thereby generating, for each of the original images and for each of the plurality of sequences, a multi-fold degraded image, wherein
the training of the untrained version of the machine-learning logic is performed on at least the original images, the plurality of sequences and their respectively generated multi-fold degraded images.

8. The method of claim 5, the first sequence being defined manually and representing a known sequence of artifact generation in a tissue staining and image acquisition workflow.

9. The method of claim 1, wherein the machine-learning logic trained for providing the image-artifact-generation logic and/or for providing the program logic configured for removing artifacts is a neural network or an autoencoder.

10. An image-correction method for tissue images depicting a biological sample, the method comprising:
receiving a digital image of the biological sample, the digital image comprising an artifact;
applying the program logic generated in accordance with claim 1 on the received digital image for generating an artifact-corrected image; and
returning the artifact-corrected image.

11. A method for providing program logic adapted to remove artifacts from digital tissue images, the method comprising:
creating first image-artifact-generation logic, the first image-artifact-generation logic being configured for specifically generating a first type of artifact, the first image-artifact-generation logic being a tissue-staining-artifact-generation logic, the tissue-staining-artifact-generation logic being a color-noise-generation-logic adapted to specifically generate artifacts consisting of optical noise of a defined color or color combination in an input image, the creating the color-noise-generation-logic including,
  specifying a color-specific salt-and-pepper function adapted to simulate tissue slides regions with residual stain, and
  creating the first image-artifact-generation logic by integrating said color-specific salt-and-pepper function into a machine-executable code;
generating, for each of a plurality of original images respectively depicting a tissue sample, a first artificially degraded image by applying the first image-artifact-generation logic on each of the original images; and
generating a program logic configured for removing artifacts from digital tissue images, the generating the program logic including training an untrained version of a first machine-learning logic that encodes a first artifacts-removal logic on the original images and their respectively generated first degraded images, and returning the trained first machine-learning logic as the program logic or as a component thereof.

12. The method of claim 11, wherein when the program logic is applied on a received digital image, the color-specific salt-and-pepper function is applied to the received digital image, the applying the color-specific salt-and-pepper function on the received digital image including,
  generating, for each pixel in the received digital image, a random value;
  specifying a salt-and-pepper noise threshold;
  determining, for each pixel in the received digital image, if the random value generated for the pixel is smaller than the salt-and-pepper noise threshold; and
  replacing the pixel with a black or white pixel, in response to the random value being smaller than the salt-and-pepper noise threshold.

13. The method of claim 11, further comprising:
generating, for each of the original images, a second artificially degraded image by applying a second image-artifact-generation logic on each of the original images, the second image-artifact-generation logic being configured for specifically generating a second type of artifact, and wherein
the generating of the program logic configured for removing artifacts further includes:
  training an untrained version of a second machine-learning logic that encodes a second artifacts-removal logic on the original images and their respectively generated second degraded images; and
  combining the trained first machine-learning logic with the trained second machine-learning logic for providing the program logic, the program logic being configured for removing artifacts of at least the first and the second artifact type.

14. The method of claim 13, wherein the second image-artifact-generation logic is A) an image-acquisition-system-specific image-artifact-generation logic or B) a tissue-staining-artifact-generation logic, the second image artifact generation logic being different from the first image-artifact-generation logic.

15. The method of claim 11, wherein the program logic is configured for removing artifacts of multiple different types, and the method further comprising:
providing, for each of the different artifact types, a respective image-artifact-generation logic configured for specifically generating a respective one of the different artifact types; and
applying, according to a first sequence, the different image-artifact-generation logics on each of the original images, whereby the image-artifact-generation logic at the first position within the first sequence takes each of the original images as input and wherein the degraded image output by said image-artifact-generation logic and any image-artifact-generation logic at a subsequent position within the first sequence is used as input image by the next one of the different image-artifact-generation logics in the first sequence, thereby generating, for each of the original images, a first multi-fold degraded image, wherein
the generating of the program logic further includes:
  training a machine-learning logic that encodes a multi-step-artifacts-removal logic, the training being performed on at least the original images and their respectively generated first multi-fold degraded images; and
  using said trained multi-artifact-machine-learning logic as the program logic or as part of the program logic, the program logic being configured for sequentially removing artifacts of each of the multiple types of artifacts.

16. The method of claim 15, further comprising:
applying, according to at least a second sequence, different image-artifact-generation logics on the original images, whereby the image-artifact-generation logic at the first position within in the second sequence takes each of the original images as input and wherein the degraded image output by said image-artifact-generation logic and any image-artifact-generation logic at a subsequent position within the second sequence is used as input image by the next one of the different image-artifact-generation logics in the second sequence, thereby generating, for each of the original images, a second multi-fold degraded image, wherein
the training of the untrained version of the machine-learning logic is performed on at least the original images and their respectively generated first and second multi-fold degraded images.

17. The method of claim 11, further comprising:
automatically creating a plurality of sequences of the different image-artifact-generation logics, each of the plurality of sequences comprising different image-artifact-generation logics at a first, a second and at least a third position by permutating the positions of the image-artifact-generation logics within the respective sequence; and
applying, for each of the plurality of sequences, the image-artifact-generation logics of said sequence on the original images, whereby the image-artifact-generation logic at the first position within in said sequence takes each of the original images as input and wherein the degraded image output by said image-artifact-generation logic and any image-artifact-generation logic at a subsequent position in said sequence is used as input image by the next one of the different image-artifact-generation logics in said sequence, thereby generating, for each of the original images and for each of the plurality of sequences, a multi-fold degraded image, wherein
the training of the untrained version of the machine-learning logic is performed on at least the original images, the plurality of sequences and their respectively generated multi-fold degraded images.

18. The method of claim 15, the first sequence being defined manually and representing a known sequence of artifact generation in a tissue staining and image acquisition workflow.

19. The method of claim 11, wherein the machine-learning logic trained for providing the image-artifact-generation logic and/or for providing the program logic configured for removing artifacts is a neural network or an autoencoder.

20. An image-correction method for tissue images depicting a biological sample, the method comprising:
receiving a digital image of the biological sample, the digital image comprising an artifact;
applying the program logic generated in accordance with claim 11 on the received digital image for generating an artifact-corrected image; and
returning the artifact-corrected image.

21. The method of claim 1, wherein, when the program logic is applied on a received digital image, the square filter is applied to the received digital image to generate a pattern of degraded squares that simulate the stitching artifact.

22. The method of claim 11, wherein, when the program logic is applied on a received digital image, the color-specific salt-and-pepper function is applied to the received digital image to selectively replace pixels in the received digital image with a pixel having a preset color.

\* \* \* \* \*